(12) United States Patent
Webster et al.

(10) Patent No.: US 11,833,071 B2
(45) Date of Patent: *Dec. 5, 2023

(54) CERVICAL COLLAR HAVING HEIGHT ADJUSTMENT

(71) Applicant: Ossur Iceland ehf, Reykjavik (IS)

(72) Inventors: Christopher Callicott Webster, Foothill Ranch, CA (US); Harry Duane Romo, Foothill Ranch, CA (US); Janaki Ram-srinivasaRao Chetlapalli, Foothill Ranch, CA (US); Jason Robert Taylor, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 65 days.

This patent is subject to a terminal disclaimer.

(21) Appl. No.: 17/343,943

(22) Filed: Jun. 10, 2021

(65) Prior Publication Data
US 2021/0298940 A1 Sep. 30, 2021

Related U.S. Application Data

(63) Continuation of application No. 15/092,282, filed on Apr. 6, 2016, now Pat. No. 11,083,616.
(Continued)

(51) Int. Cl.
*A61F 5/055* (2006.01)

(52) U.S. Cl.
CPC .................................. *A61F 5/055* (2013.01)

(58) Field of Classification Search
CPC .... A61F 5/055; A61F 5/01; A61F 5/05; A61F 5/05883; A61F 5/04; A61F 5/37; A61F 13/12; A61F 13/128; Y10S 128/23; A41D 13/0512; A61N 2005/1097; A61D 2003/003
(Continued)

(56) References Cited

U.S. PATENT DOCUMENTS 2,088,207 A 7/1937 Kaiser
2,102,069 A 12/1937 Hanicke
(Continued)

FOREIGN PATENT DOCUMENTS

CN 1646071 A 7/2005
CN 2933343 Y 8/2007
(Continued)

OTHER PUBLICATIONS

Office Action from corresponding CN Application No. 201780057654.X, dated Oct. 29, 2020.
(Continued)

*Primary Examiner* — Caitlin A Carreiro
(74) *Attorney, Agent, or Firm* — WORKMAN NYDEGGER

(57) ABSTRACT

A cervical collar has a height adjustment system between upper and lower parts forming an anterior component for increasing height of the anterior component inclusive of a tracheal opening. The anterior component is arranged to permit the use of known mandibular and occipital supports in the cervical collar to maintain their functionality, comfort and fit, including their anatomical contours and connection to the height adjusted anterior component.

19 Claims, 13 Drawing Sheets

Related U.S. Application Data

(60) Provisional application No. 62/143,630, filed on Apr. 6, 2015.

(58) Field of Classification Search
USPC ....... 602/5, 18; 128/DIG. 23, 845, 846, 869; D24/191; 119/815
See application file for complete search history.

(56) References Cited

U.S. PATENT DOCUMENTS

| | | |
|---|---|---|
| 2,735,424 A | 2/1953 | Benjamin |
| 2,791,999 A | 5/1954 | Bustamante |
| 2,801,630 A | 8/1957 | Moore |
| 2,806,471 A | 11/1957 | Breese |
| 2,818,063 A | 12/1957 | Smith et al. |
| 2,820,455 A | 1/1958 | Hall |
| 2,911,970 A | 11/1959 | Bartels |
| D188,302 S | 6/1960 | Monfardini |
| 3,024,784 A | 3/1962 | Monfardini |
| 3,027,894 A | 4/1962 | Moore |
| 3,042,027 A | 7/1962 | Monfardini |
| 3,050,052 A | 8/1962 | Grassl |
| 3,060,930 A | 10/1962 | Grassl |
| 3,075,521 A | 1/1963 | Grassl |
| 3,135,256 A | 6/1964 | Gruber |
| 3,177,869 A | 4/1965 | Bartels |
| D203,018 S | 11/1965 | Helferich |
| 3,285,243 A | 11/1966 | Yellin |
| 3,285,244 A | 11/1966 | Cottrell |
| 3,306,284 A | 2/1967 | McKinley |
| 3,313,297 A | 4/1967 | Applegate et al. |
| 3,320,950 A | 5/1967 | McElvenny |
| 3,504,667 A | 4/1970 | McFarlane |
| 3,512,523 A | 5/1970 | Barnett |
| 3,756,226 A | 9/1973 | Calabrese et al. |
| 3,916,884 A | 11/1975 | Attenburrow |
| 3,916,885 A | 11/1975 | Gaylord, Jr. |
| 4,099,523 A | 7/1978 | Lowrey |
| 4,173,973 A | 11/1979 | Hendricks |
| 4,205,667 A | 6/1980 | Gaylord, Jr. |
| 4,325,363 A | 4/1982 | Berkeley |
| 4,401,111 A | 8/1983 | Blackstone |
| 4,413,619 A | 11/1983 | Garth |
| D278,747 S | 5/1985 | Peach, Jr. |
| 4,520,801 A | 6/1985 | Lerman |
| 4,538,597 A | 9/1985 | Lerman |
| 4,562,833 A | 1/1986 | Pujals, Jr. |
| 4,582,051 A | 4/1986 | Greene et al. |
| 4,628,913 A | 12/1986 | Lerman |
| 4,643,174 A | 2/1987 | Horiuchi |
| 4,677,969 A | 7/1987 | Calabrese |
| 4,702,233 A | 10/1987 | Omicioli |
| 4,708,129 A | 11/1987 | Pujals, Jr. |
| 4,712,540 A | 12/1987 | Tucker et al. |
| 4,732,144 A | 3/1988 | Cunanan |
| 4,745,922 A | 5/1988 | Taylor |
| 4,827,915 A | 5/1989 | Gorsen |
| 4,854,306 A | 8/1989 | Pujals, Jr. |
| 4,886,052 A | 12/1989 | Calabrese |
| 4,940,043 A | 7/1990 | Burns et al. |
| 4,955,368 A | 9/1990 | Heimann |
| 4,987,891 A | 1/1991 | Gaylord, Jr. et al. |
| D314,623 S | 2/1991 | Calabrese et al. |
| 5,005,563 A | 4/1991 | Veale |
| 5,038,759 A | 8/1991 | Morgenstern |
| 5,058,572 A | 10/1991 | Schmid et al. |
| 5,060,637 A | 10/1991 | Schmid et al. |
| 5,097,824 A | 3/1992 | Garth |
| 5,156,588 A | 10/1992 | Marcune et al. |
| 5,180,361 A | 1/1993 | Moore et al. |
| 5,201,702 A | 4/1993 | Mars |
| 5,215,517 A | 6/1993 | Stevenson et al. |
| 5,230,698 A | 7/1993 | Garth |
| 5,275,581 A | 1/1994 | Bender |
| 5,302,170 A | 4/1994 | Tweardy |
| RE34,714 E | 8/1994 | Burns et al. |
| 5,346,461 A | 9/1994 | Heinz et al. |
| 5,366,438 A | 11/1994 | Martin, Sr. |
| 5,385,535 A | 1/1995 | McGuinness |
| 5,433,696 A | 7/1995 | Osti |
| 5,437,612 A | 8/1995 | Moore et al. |
| 5,437,617 A | 8/1995 | Heinz et al. |
| 5,445,602 A | 8/1995 | Grim et al. |
| D368,527 S | 4/1996 | Brooke |
| D369,660 S | 5/1996 | Myoga |
| 5,520,619 A | 5/1996 | Martin |
| RE35,290 E | 7/1996 | Druskoczi |
| 5,588,957 A | 12/1996 | Martin, Sr. |
| 5,593,382 A | 1/1997 | Rudy, Jr. et al. |
| 5,622,529 A | 4/1997 | Calabrese |
| 5,624,387 A | 4/1997 | McGuinness |
| D379,232 S | 5/1997 | Brooke |
| 5,632,722 A | 5/1997 | Tweardy et al. |
| 5,688,229 A | 11/1997 | Bauer |
| 5,716,335 A | 2/1998 | Iglesias et al. |
| 5,728,054 A | 3/1998 | Martin |
| D393,718 S | 4/1998 | Traut et al. |
| 5,785,670 A | 7/1998 | Hiebert |
| 5,788,658 A | 8/1998 | Islava |
| 5,795,315 A | 8/1998 | Traut et al. |
| 5,797,713 A | 8/1998 | Tweardy et al. |
| 5,797,863 A | 8/1998 | Kohnke |
| RE35,940 E | 10/1998 | Heinz et al. |
| 5,865,773 A | 2/1999 | Koledin |
| 5,904,662 A | 5/1999 | Myoga |
| 5,934,599 A | 8/1999 | Hammerslag |
| 5,964,722 A | 10/1999 | Goralnik et al. |
| 5,976,098 A | 11/1999 | Sereboff |
| 5,993,403 A | 11/1999 | Martin |
| 6,027,467 A | 2/2000 | Nakamura et al. |
| 6,036,664 A | 3/2000 | Martin, Sr. et al. |
| D422,710 S | 4/2000 | Maynard |
| 6,045,522 A | 4/2000 | Grober |
| 6,045,523 A | 4/2000 | Donaldson |
| 6,050,965 A | 4/2000 | Pillai |
| 6,056,711 A | 5/2000 | Domamski et al. |
| 6,058,517 A | 5/2000 | Hartunian |
| RE36,745 E | 6/2000 | Rudy, Jr. et al. |
| 6,071,255 A | 6/2000 | Calabrese |
| 6,071,256 A | 6/2000 | Lam |
| 6,090,058 A | 7/2000 | Traut et al. |
| 6,165,146 A | 12/2000 | Giebeler |
| 6,183,501 B1 | 2/2001 | Latham |
| 6,202,953 B1 | 3/2001 | Hammerslag |
| 6,245,033 B1 | 6/2001 | Martin |
| 6,254,560 B1 | 7/2001 | Tweardy et al. |
| 6,308,345 B1 | 10/2001 | Williams, Jr. |
| 6,289,558 B1 | 11/2001 | Hammerslag |
| 6,315,746 B1 | 11/2001 | Garth et al. |
| 6,423,020 B1 | 7/2002 | Koledin |
| 6,458,090 B1 | 10/2002 | Walpin |
| 6,494,854 B1 | 12/2002 | Visness et al. |
| D475,139 S | 5/2003 | Myoga |
| 6,632,722 B2 | 10/2003 | Fujiwara et al. |
| 6,663,581 B1 | 12/2003 | Calabrese |
| 6,663,630 B2 | 12/2003 | Farley et al. |
| 6,726,643 B1 | 4/2004 | Martin |
| 6,733,469 B2 | 5/2004 | Miyaji et al. |
| 6,740,055 B2 | 5/2004 | Dominguez |
| 6,770,046 B2 | 8/2004 | Hansen |
| 6,872,188 B2 | 3/2005 | Caille et al. |
| 6,913,584 B2 | 7/2005 | Rudy, Jr. et al. |
| 6,921,376 B2 | 7/2005 | Tweardy et al. |
| 6,926,686 B2 | 8/2005 | Cheatham |
| 7,018,351 B1 | 3/2006 | Iglesias et al. |
| 7,041,073 B1 | 5/2006 | Patron |
| 7,070,573 B2 | 7/2006 | Axelsson |
| 7,090,652 B2 | 8/2006 | Santelli, Jr. |
| 7,090,653 B2 | 8/2006 | Moeller |
| 7,128,724 B2 | 10/2006 | Marsh |
| 7,141,031 B2 | 11/2006 | Garth et al. |
| 7,198,610 B2 | 4/2007 | Ingimundarson et al. |
| D542,919 S | 5/2007 | Leatt |
| 7,258,677 B2 | 8/2007 | Rudy, Jr. et al. |

(56) References Cited

U.S. PATENT DOCUMENTS

| | | |
|---|---|---|
| D552,742 S | 10/2007 | Leatt |
| 7,291,121 B2 | 11/2007 | Rudy, Jr. et al. |
| 7,297,127 B2 | 11/2007 | Lee et al. |
| 7,311,686 B1 | 12/2007 | Iglesias et al. |
| 7,371,221 B1 | 5/2008 | Baker |
| 7,371,222 B2 | 5/2008 | Heinz et al. |
| 7,399,288 B2 | 7/2008 | Chao |
| 7,442,176 B2 | 10/2008 | Cojbasic |
| D609,815 S | 2/2010 | Patterson |
| 7,674,234 B2 | 3/2010 | Calco et al. |
| D616,555 S | 5/2010 | Thorgilsdottir et al. |
| D616,996 S | 6/2010 | Thorgilsdottir et al. |
| D616,997 S | 6/2010 | Thorgilsdottir et al. |
| D617,907 S | 6/2010 | Waller |
| 7,815,585 B2 | 10/2010 | Vollbrecht |
| 7,846,117 B2 | 12/2010 | Leatt et al. |
| D631,167 S | 1/2011 | Leatt et al. |
| 7,878,995 B2 | 2/2011 | Harty |
| 7,896,827 B2 | 3/2011 | Ingimundarson et al. |
| 7,981,068 B2 | 7/2011 | Thorgilsdottir et al. |
| D643,978 S | 8/2011 | Abajo Alonso et al. |
| D644,331 S | 8/2011 | Sandhu |
| D644,332 S | 8/2011 | Sandhu |
| 7,992,261 B2 | 8/2011 | Hammerslag et al. |
| D647,623 S | 10/2011 | Thorgilsdottir et al. |
| D647,624 S | 10/2011 | Thorgilsdottir et al. |
| 8,038,635 B2 | 10/2011 | Dellanno |
| 8,038,636 B2 | 10/2011 | Thorgilsdottir et al. |
| D659,842 S | 5/2012 | Donaldson et al. |
| D662,597 S | 6/2012 | Chang |
| 8,216,167 B2 | 7/2012 | Garth et al. |
| D666,302 S | 8/2012 | Joseph |
| 8,257,292 B2 | 9/2012 | Linares |
| 8,545,423 B2 | 8/2013 | Patron |
| D692,568 S | 10/2013 | Chiang et al. |
| D693,014 S | 11/2013 | Chiang et al. |
| 8,679,044 B2 | 3/2014 | Thorgilsdottir et al. |
| 8,932,243 B2 | 1/2015 | Calabrese |
| 9,132,027 B2 | 9/2015 | Calco |
| D767,825 S | 9/2016 | Georgeson et al. |
| 9,713,546 B2 | 7/2017 | Thorsteinsdottir et al. |
| 10,675,173 B2 | 6/2020 | Thorsteinsdottir et al. |
| 11,083,616 B2 * | 8/2021 | Webster ............... A61F 5/055 |
| 2002/0138028 A1 | 9/2002 | Rudy, Jr. et al. |
| 2002/0156408 A1 | 10/2002 | Cheatham |
| 2002/0156409 A1 | 10/2002 | Lee et al. |
| 2002/0169401 A1 | 11/2002 | Walpin |
| 2002/0173737 A1 | 11/2002 | Miyaji et al. |
| 2003/0055367 A1 | 3/2003 | Dominguez |
| 2003/0060744 A1 | 3/2003 | Caille et al. |
| 2003/0181838 A1 | 9/2003 | Garth |
| 2004/0039318 A1 | 2/2004 | Santelli, Jr. |
| 2005/0101896 A1 | 5/2005 | Calabrese |
| 2007/0027418 A1 | 2/2007 | Calco et al. |
| 2007/0073203 A1 | 3/2007 | Moenning et al. |
| 2007/0270728 A1 | 11/2007 | Chao |
| 2009/0247918 A1 | 10/2009 | Patron |
| 2010/0137768 A1 | 6/2010 | Thorgilsdottir et al. |
| 2010/0268139 A1 | 10/2010 | Garth |
| 2010/0298748 A1 | 11/2010 | Rosenfeld et al. |
| 2011/0034844 A1 | 2/2011 | Thorgilsdottir et al. |
| 2011/0066094 A1 | 3/2011 | Thorgilsdottir et al. |
| 2011/0224591 A1 | 9/2011 | Thorgilsdottir et al. |
| 2012/0053499 A1 | 3/2012 | Donaldson et al. |
| 2012/0130295 A1 | 5/2012 | Haider |
| 2012/0165712 A1 | 6/2012 | Calabrese |
| 2013/0060179 A1 * | 3/2013 | Modglin ............... A61F 5/01 602/18 |
| 2013/0281899 A1 | 10/2013 | Suarez et al. |
| 2013/0281900 A1 * | 10/2013 | Suarez ............... A61F 5/055 602/18 |
| 2013/0310722 A1 | 11/2013 | Thorsteinsdottir et al. |
| 2014/0012172 A1 | 1/2014 | Calco |
| 2014/0107551 A1 | 4/2014 | Modglin |
| 2014/0323938 A1 | 10/2014 | Suarez et al. |
| 2015/0216708 A1 * | 8/2015 | Garth ............... A61F 5/055 602/18 |
| 2016/0008158 A1 | 1/2016 | Martin et al. |
| 2017/0246022 A1 | 8/2017 | Calco et al. |
| 2017/0252198 A1 | 9/2017 | Thorsteinsdottir et al. |
| 2018/0078400 A1 | 3/2018 | Hsu et al. |
| 2018/0078401 A1 | 3/2018 | Hsu et al. |
| 2020/0281754 A1 | 9/2020 | Thorsteinsdottir et al. |

FOREIGN PATENT DOCUMENTS

| | | | |
|---|---|---|---|
| CN | 201150587 Y | 11/2008 | |
| CN | 201602923 U | 10/2010 | |
| CN | 102227196 A | 10/2011 | |
| CN | 202015274 U | 10/2011 | |
| CN | 204655220 U | 9/2015 | |
| CN | 105120808 A | 12/2015 | |
| DE | 19547115 A1 | 6/1997 | |
| DE | 19849302 A1 | 4/2000 | |
| DE | 100 57 286 A1 | 5/2002 | |
| EP | 1738724 A1 | 1/2007 | |
| EP | 2653139 A1 | 10/2013 | |
| EP | 2886088 A1 | 6/2015 | |
| EP | 2886088 A1 * | 6/2015 | ............ A61F 5/055 |
| FR | 2 814 362 A1 | 3/2002 | |
| GB | 2 165 157 A | 4/1986 | |
| GB | 2 453 996 A | 4/2009 | |
| JP | 2007-330808 A | 12/2007 | |
| WO | 94/09728 A1 | 5/1994 | |
| WO | 95/22304 A1 | 8/1995 | |
| WO | 96/40018 A1 | 12/1996 | |
| WO | 9843568 A1 | 10/1998 | |
| WO | 2014102340 A1 | 7/2014 | |

OTHER PUBLICATIONS

International Search Report form PCT Application No. PCT/US2016/026222, dated Jul. 14, 2016.

Partial International Search Report from PCT Application No. PCT/US2017/050206, dated Dec. 5, 2017.

Product Brochure, "Capital Collar Enhanced," DeRoyal, 2014, 2 Pages.

Product Brochure, "Instructions for Use Eclipse Cervical Collar," VQ OrthoCare, 2015, 2 Pages.

Product Brochure, "Miami J Advanced By OSSUR," www.ossur.com, 2012, 4 Pages.

Product Brochure, "Miami J Cervical Collar," www.ossur.com, 1 Page.

Product Brochure, "Proglide Cervical Collar," OPTEC, www.optecusa.com, 1 Page.

Product Brochure, "Vista Upper Spine," Aspen Medical Products, 2015, 6 Pages.

"Range-of-Motion Restriction and Craniofacial Tissue-Interface Pressure From Four Cervical Collars", The Journal of Trauma Injury, Infection, and Critical Care, vol. 63, No. 5, Nov. 2007, pp. 1120-1126.

"Ossur Is Immobilization", www.ossur.com, 2008, pp. 1-16.

"Miami J Patient Care Handbook", www.ossur.com, 2010, pp. 1-16.

Jacobson et al. "Improving Practice Efforts to Reduce Occipital Pressure Ulcers", Journal of Nursing Care Quality, vol. 23, No. 3, 2008, pp. 283-288.

Bell et al. "Assessing Range of Motion to Evaluate the Adverse Effects of Ill-Fitting Cervical Orthoses", The Spine Journal, vol. 9, 2009, pp. 225-231.

Karason et al. "Evaluation of Clinical Efficacy and Safety of Cervical Trauma Collars: Differences in Immobilization, Effect on Jugular Venous Pressure and Patient Comfort", Scandinavian Journal of Trauma, Resuscitation and Emergency Medicine, 2014, pp. 1-7.

Levangie et al., "Joint Structure and Function: A Comprehensive Analysis", Fourth Edition, Chapter 4: The Vertebral Column, 2005 F.A. Davis Company, Philadelphia, PA, pp. 161-164.

Hsu et al., AAOS Atlas of Orthoses and Assistive Devices, Mosby, Elsevier Fourth Edition, 2008, Philadelphia, PA, p. 117-122.

(56) References Cited

OTHER PUBLICATIONS

International Search Report and Written Opinion from PCT Application No. PCT/US2009/006335, dated Mar. 11, 2010, 8 pages.
Product Information Sheet, Philadelphia Tracheotomy Collar, obtained from www.ossur.com, prior to Aug. 6, 2010, 1 page.
Product Information Sheet, Platazote Sheets, WBC Industries, obtained from www.wbcindustries.com prior to Aug. 6, 2010, 2 pages.
International Search Report and Written Opinion from PCT Application No. PCT/US2010/002199, dated Dec. 27, 2010, 9 Pages.
Chinese Search Report from corresponding CN Application Serial No. 200980147713.8, dated Dec. 6, 2012.
European Search Report from corresponding EP Application Serial No. 13165274.5, dated Jul. 17, 2013.
International Search Report from PCT Application No. PCT/US2013/041586, dated Oct. 1, 2013.

\* cited by examiner

CERVICAL COLLAR HAVING HEIGHT ADJUSTMENT

CROSS-REFERENCE TO RELATED APPLICATIONS

This application is a continuation of U.S. application Ser. No. 15/092,282, filed Apr. 6, 2016, which claims the benefit of U.S. provisional application No. 62/143,630, filed Apr. 6, 2015. This disclosure incorporates by reference U.S. Pat. No. 5,632,722, granted May 27, 1997, U.S. Pat. No. 6,254,560, granted Jul. 3, 2001, U.S. Pat. No. 7,981,068, granted Jul. 19, 2011, U.S. Pat. No. 8,038,636, granted Oct. 18, 2011, and U.S. Pat. No. 8,679,044, granted Mar. 25, 2014.

FIELD OF THE DISCLOSURE

The present disclosure relates to an orthopedic device, and more specifically to cervical collars having height adjustability at a front part, while providing a platform for securing known other components of a cervical collar thereto without modifying their anatomical contours and connection to the height adjusted components.

BACKGROUND

Cervical collars are used for treating conditions of the neck and the cervical spine by cervical spine immobilization. These collars may handle whiplash and other such injuries, where support for the head and neck of the patient is needed, and function to partially immobilize the head and neck of the patient and relieve spasm or strain to which the neck muscles of the patient might be subjected by transferring weight or force from the head of the patient to the shoulders or adjacent areas of the patient. Other collars may be arranged for complete or near complete immobilization of the head and neck of the patient to reduce risk of secondary damage to the spinal cord.

A challenge in designing a cervical collar is balancing desired immobilization with user comfort, such as venous pressure. Immobilization may be measured by five planes of movement, including the degree of flexion, extension, lateral tilt to right and left, and rotation of the neck to right and left, and is considered generally as cervical range of motion (CROM).

Unfortunately, many patients using cervical collars develop decubitus or decubitus ulcers (also known as bed sores, pressure sores, or trophic ulcers) when wearing cervical collars. These ailments, which involve a breakdown of tissue overlying a bone, arise when tissues overlying a bony prominence are subjected to prolonged pressure against an object such as a cervical collar. In addition to affecting superficial tissues such as the skin, decubitus and decubitus ulcers also can affect muscle and bone. Restrictive collars are the root causes of skin breakdown in the trauma population. As pressure-ulcers are among the most common, yet serious and costly, complications of routine spinal immobilization, it is desirable to provide cervical collars that minimize the probability of ulcers.

Moisture and pressure are two of the major factors which contribute to the formation of decubitus. Once a decubitus ulcer forms, there is no good method of determining the extent of tissue damage. Once started, decubitus can continue to progress through the skin and fat tissue to muscle and eventually to bone, and is very difficult to treat and arrest. In extreme cases, surgical replacement of bone, muscle and skin are required to restore that portion of the body of the patient where decubitus has formed.

Consequently, it is desirable to eliminate or at least minimize the effect of pressure points when using cervical collars. The likelihood of contracting decubitus can be greatly reduced by a more even distribution of pressure to a number of parts of the body of the patient.

Multiple studies have evaluated CROM and likelihood of tissue-interface pressure (TIP) exerted by commercially-available cervical collars. One of the known commercial collars that has proven successful at striking the balance of minimal TIP and most restriction of CROM is the Miami J collar (Össur, hf, Reykjavik, Iceland). Multiple studies have validated the features of the Miami J, including: Tescher, A. N. et al. Range-of-motion restriction and craniofacial tissue-interface pressure from four cervical collars. *Journal of Trauma-Injury Infection & Critical Care:* 2007; 63; 5; 1120-1126; Jacobson, T. M. et al. Efforts to reduce occipital pressure ulcers. *Journal of Nursing Care Quality;* 2008; 23; 3; 283-288; Karason, S. et al. Evaluation of clinical efficacy and safety of cervical trauma collars: differences in immobilization, effect on jugular pressure and patient comfort. *Scandinavian Journal of Trauma, Resuscitation and Emergency Medicine.* 2014. 22:37.

The Miami J collar is also described in U.S. Pat. No. 5,632,722, granted May 27, 1997; U.S. Pat. No. 6,254,560, granted Jul. 3, 2001; U.S. Pat. No. 6,921,376, granted Jul. 26, 2005. Variations of the Miami J collar, embodying the Miami J Advance collar, are described in U.S. Pat. No. 7,981,068, granted Jul. 19, 2011, and U.S. Pat. No. 8,679,044, granted Mar. 25, 2014.

A feature, preferably included in cervical collars to overcome limited adaptability to accommodate the body of the patient and the particular ailment prompting the need for wearing a cervical collar, is the facility for adjusting the relative positions of various components of the cervical collar. Part of the effectiveness of the Miami J collar is due to its ability for customization to different anatomical sizes of users.

As taught in U.S. Pat. No. 6,254,560, the Miami J collar has supports that enable customized pressure distribution and avoid skin breakdown. For example, a front part of the Miami J collar has an adjustable mandibular support mounted to the sternum brace by means which permit relative sliding movement between the mandibular support and the sternum brace. The back part of the Miami J collar has an occipital support mounted to a back support by means which permit relative sliding movement between the occipital support and the back support. The shape of the mandibular support and occipital support are anatomically optimized for superior immobilization and patient comfort.

Both the mandibular support and the occipital support of the Miami J collar are uniquely anatomically shaped to maximize comfort and immobilization while minimizing pressure on the user. Because mandibular support and the occipital support of the Miami J collar are clinically proven, it is desired that any improvements over the current Miami J collar provide means for preserving the function and shape of the mandibular support and occipital support of the current Miami J collar.

SUMMARY

Embodiments of the disclosure relate to a cervical collar having a height adjustment system between upper and lower parts forming an anterior component, which permit the use of known mandibular and occipital supports in the cervical collar to maintain their functionality, comfort and fit, including their anatomical contours and connection to the height adjusted components. The height adjustment system is arranged for adjusting the chin height in a simple and effective manner that limits or mitigates tampering with the height while the collar is worn. The height adjustment system preferably includes using incremental height adjustment so that the height may be locked at a desired height setting. The height adjustment system may be arranged to allow usage in existing collar designs, such as the Miami J or Miami J Advance collars, without substantially altering the shape and function of the mandibular and posterior component including an occipital support.

The height adjustment system mitigates or eliminates the need for pre-sizing methods, and is provided in a simplified manner to enable many height settings customizable for different users. The height adjustment system enables use of known mandibular and posterior supports, which have been on the market for many years and have been used to serves many users of cervical collars.

The height adjustment system allows for improved placement and configuration of a cervical collar on patients of different heights. The mandibular support and posterior component can be properly fitted against the chin and head of a patient by a clinician, followed by the extension of the anterior component against the patient's chest. Likewise the anterior component may be placed against the patient's chest and the mandibular support and posterior component can then be extended to the chin and head of the patient. The height setting can then be locked at the desired height setting by the clinician to ensure a proper fit for the user.

The shape and function of the anterior component may resemble the cervical collar described in U.S. Pat. Nos. 6,632,722 and 6,254,560. The anterior component may include features taught in U.S. Pat. Nos. 7,981,068, 8,038,636 and 8,679,044. Likewise, a posterior component for coupling to the anterior component to form a circumferential collar may be found in any of the aforementioned patents incorporated by reference.

BRIEF DESCRIPTION OF THE DRAWINGS

These and other features, aspects, and advantages of the present disclosure will become better understood regarding the following description, appended claims, and accompanying drawings.

Figure 1:
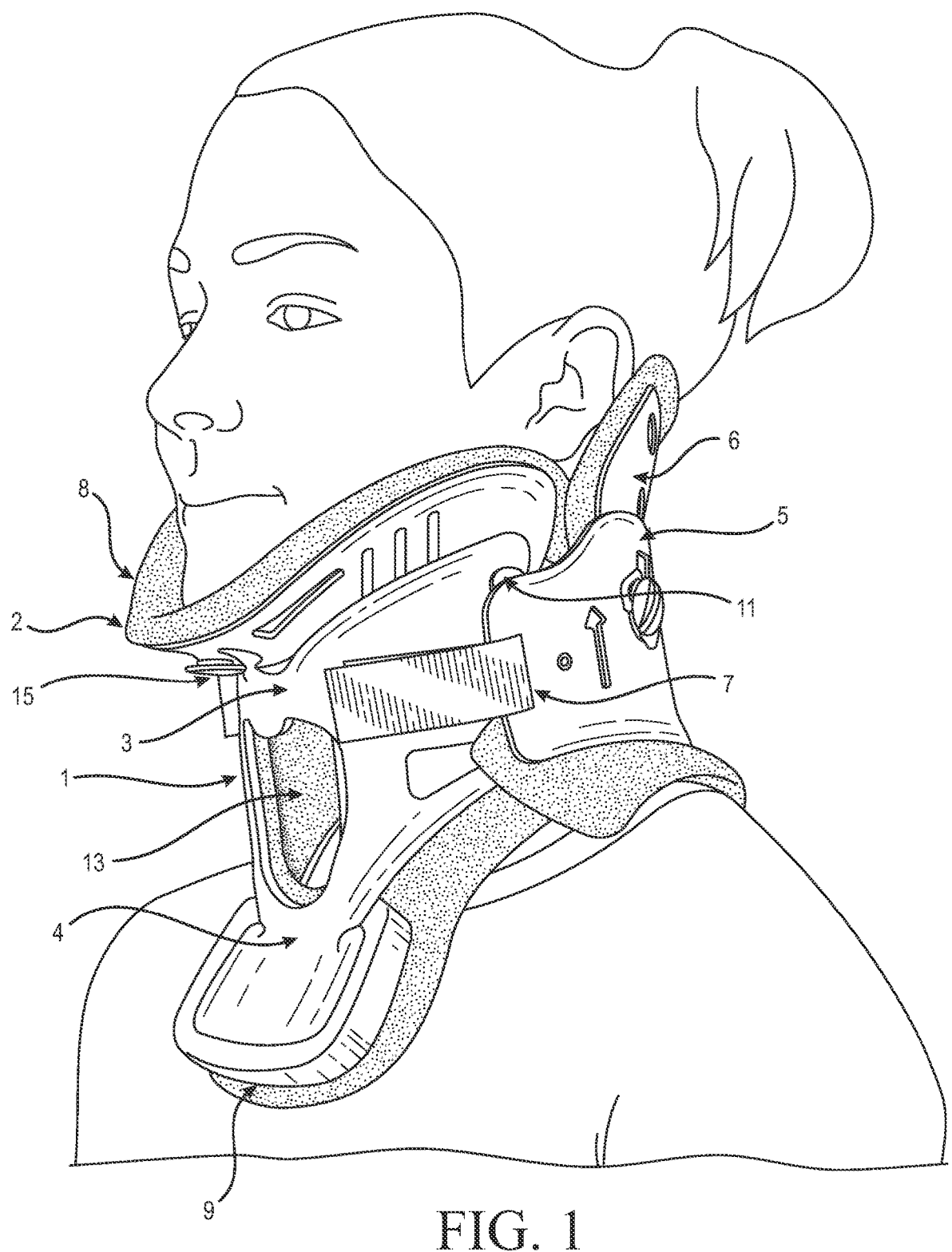
FIG. 1 is a perspective view of a known collar under the commercial name Miami J.

The drawing figures are not drawn to scale, but instead are drawn to provide a better understanding of the components, and are not intended to be limiting in scope, but to provide exemplary illustrations.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

It will be understood that, unless a term is defined in this disclosure to possess a described meaning, there is no intent to limit the meaning of such term, either expressly or indirectly, beyond its plain or ordinary meaning.

While the foregoing embodiments have been described and shown, alternatives and modifications of these embodiments, such as those suggested by others may be made to fall within the scope of the invention. While the cervical collar has been described in combination with collar parts, it will be understood that the principles described may be extended to other types of orthopedic and prosthetic devices.

Reference characters are provided in the claims for explanatory purposes only and are not intended to limit the scope of the claims or restrict each claim limitation to the element shown in the drawings and identified by the reference character.

A. Components for Use with Following Embodiments

FIG. 1 exemplifies the known Miami J collar 1, as taught in the aforementioned patents and publications, particularly U.S. Pat. Nos. 5,632,722 and 6,254,560. The collar 1 includes the mandibular, jaw or chin support 2 that secures and rests upon an anterior component 3 of the collar. The mandibular support 2 is arranged for sliding movement with the anterior component 3 and for locking therewith by a side adjustment connection 11 and a central tab 15. The mandibular support 2 preferably has continuous padding 8 along a surface adjacent the user's jaw.

The anterior component 3 defines a sternum part 4, forming an extension adapted to extend below the clavicle of a user and adapted to rest against the sternum. The sternum part 4 carries a sternum pad 9 to avoid decubitus over long periods of wear of the collar. In addition to the sternum pad 9, the anterior part 3 likewise includes padding located along the surface facing the user.

The Miami J may be used by user's who have injuries other than those for which the cervical collar is most commonly used. The anterior component 3 forms an opening 13 which allows for access to the throat of the user, although because the anterior component is unitary and monolithic, the size of the opening 13 remains fixed.

The collar 1 includes a posterior component comprising lower and upper parts 5, 6, with the upper part serving as an occipital support. Both the lower and upper parts 5, 6 preferably include continuous padding, with the lower part intended to rest upon the back of the user, and the upper part intended to rest against the occiput of the head. The lower and upper parts 5, 6 are preferably attached for relative sliding movement between relative positions of the lower and upper parts so as to allow for different head sizes and proper and even pressure distribution across the body of the user.

Alternatively, although not shown, the posterior component may be unitary and monolithic in that it resembles the posterior component taught by U.S. Pat. No. 7,981,068 and found in the Miami J Advance collar. For example, the posterior component is an anatomically configured 3D support contiguously formed with resilient or compliant edges. The support includes slots to provide ventilation and/or additional resilience or flexibility. The support portion also includes an anatomically shaped flared section that is shaped to correspond to and support an anatomical portion of a wearer, for example, the occipital region.

Both the mandibular support, and the anterior and posterior components are generally symmetrical about a vertical center line, and may be formed from rigid or semi-rigid plastic. The material forming the mandibular support, and the anterior and posterior components, may be flexible prior to donning the collar, but sufficiently rigid once the collar is donned to resist yielding due to weight exerted by the user.

A fastener 7 is used to secure the anterior and posterior components to one another. For example, the fastener 7 comprises cooperating hook-and-loop attachments on the anterior and posterior components, with a strap bearing hook material extending from the posterior component and loop or hook receiving elements located on the anterior component.

Each of the following embodiments is arranged to receive the mandibular support and posterior component of the Miami J collar, or the posterior component of the Miami J Advance collar in order to preserve the clinically recognized superior immobilization and comfort provided by the existing collars. It will be noted, however, that the following embodiments are not restricted to only the mandibular support and posterior component of the Miami J and Miami J Advance collars, but can receive other mandibular support and posterior components of other known collars or those designed for each of the embodiments.

The height adjusted anterior component is arranged to preserve the anatomical contour and function of the known mandibular support and posterior component, despite the height adjustment of the anterior component and the tracheal opening thereof. The embodiments may have a varying height adjustment in that a center portion of the collar about the tracheal opening and generally along a vertical center line may increase greater in height than along side portions of the anterior component proximate the connection to the posterior component. An example, although not limiting, is a 3:1 height difference at the center portion relative to the side portions.

While the embodiments may be associated with varying neck lengths among users, the sternal contour of users may likewise vary. The varying sternal contours of users may be resolved by positioning of the sternal contour, which may be achieved by adjusting the tracheal opening height or the height generally of the collar. While anatomical vertebral height and neck length plays a role in adjustment of the collar, the alignment of the spinal segments also has an effect in overall neck "length". i.e., a more kyphotic or flexed neck position "shortens" an otherwise anatomically longer or taller neck.

As noted above, another factor relating to the dimension of the cervical collar is the sternal contour. For instance, a patient with a very barrel chested individual (having a more horizontal sternal contour) may have the distal most dimension of the sternal extension of the brace contact considerably closer to the mandible than the patient with a very vertical sternum.

In all situations suggested above, mandible dimensions would be relatively the same, it is the orientation of the neck elements and its attachment to and the contour of the sternal segment that plays the largest role in overall collar height adjustment. The mechanism affording mandible and sternal height adjustment can accommodate the varying contours and dimensions.

B. Anterior Component Embodiments and Associated Components

Figure 2:
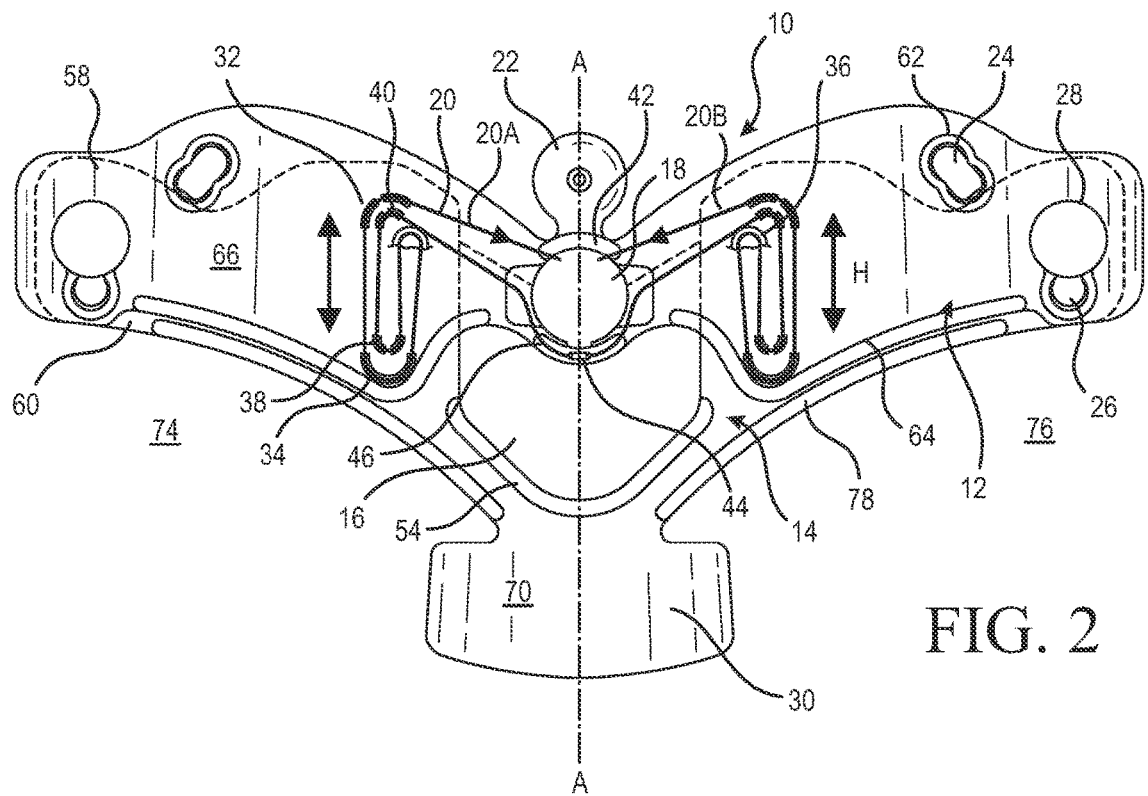
FIG. 2 is a front elevational view showing an embodiment of a cervical collar.
Figure 3:
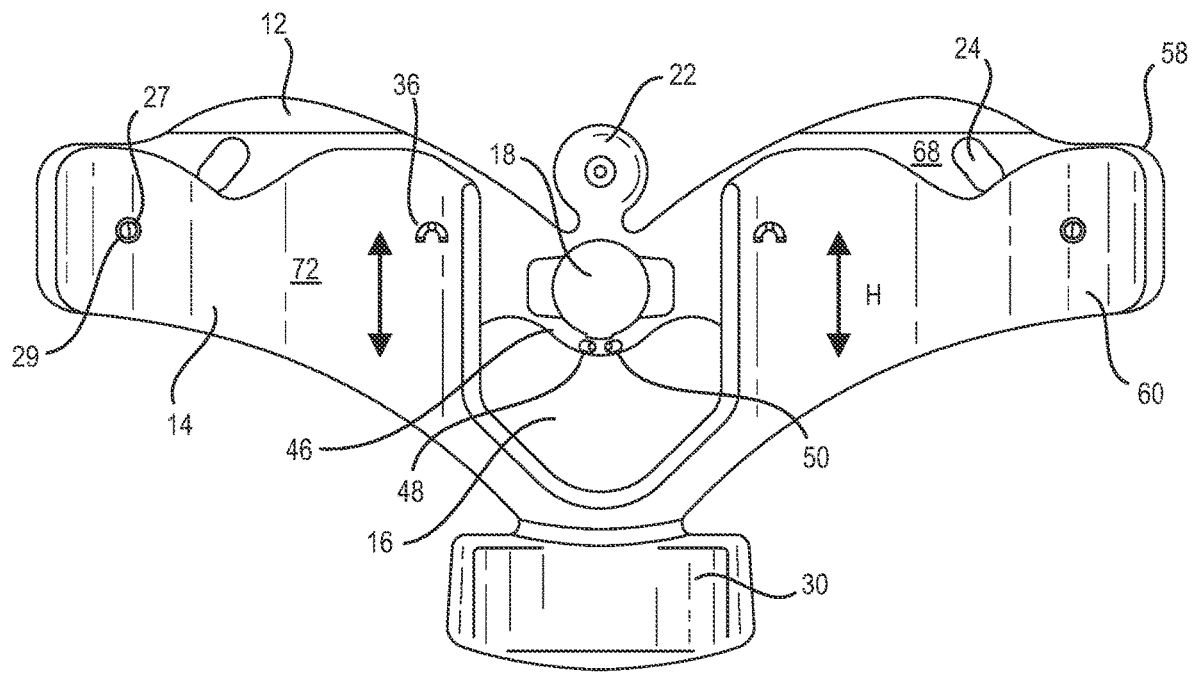
FIG. 3 is a rear elevational view showing the embodiment of FIG. 2.

As shown in FIGS. 2 and 3, an anterior component 10 is arranged for height adjustment between upper and lower parts 12, 14. A tensioning device 18 is connected to the upper part 12, and at least one cable 20 engages between the upper and lower parts 12, 14 and is arranged to be shortened or lengthened relative to the upper and lower parts 12, 14 by the tensioning device 18 to move the lower part 14 relative to the upper part 12. The tensioning device 18 is preferably mounted on an outer surface 66 of the upper part 12.

The anterior component 10 further defines a tracheal opening 16 centrally located on the anterior component 10. The tracheal opening 16 is defined in part by a peripheral segment 44 of the upper part 12 and a peripheral segment 54 of the lower part 14. A height of the tracheal opening 16 varying according to a length of the cable 20. The lower part 14 defines a sternal support 30 extending downwardly below and beyond a lower periphery 64 of the upper part 12.

To secure to a mandibular support, the anterior component 10 defines a central tab 22 generally along a vertical centerline A-A and side adjustment connections 24, as in known collars. The side adjustment connections define a female component 62 arranged at an oblique angle relative to the vertical centerline A-A to enable adjustment of the mandibular support relative to the anterior component 10.

As evident from FIGS. 2 and 3, the anterior component preserves the general contours known in the Miami J collar, particularly the peripheral outline of the anterior component of both the upper and lower parts 12, 14, which enables easy attachment to the known mandibular support and posterior component.

The upper and lower parts 12, 14 are secured to one another at wing portions 58, 60. A side height mechanism secures the wing portions 58, 60 to one another and permits height adjustment of the wing portions 58, 60 relative to one another. The side height mechanism includes a female component 26 formed by the upper part 12 and is arranged generally parallel to a vertical centerline A-A of the anterior component 10. The side height mechanism includes a fastener unit 28 adapted to selectively secure along a portion of a height of the female component 26 and secure to the lower part 14. For example, a tip 29 of the fastener unit 28 engages the lower part 14 at an aperture 27 formed by the lower part 14.

A plurality of guides is formed by the upper and lower parts 12, 14 for guiding the cable 20. The upper part 12 forms upper and lower guides 32, 34, 38, 40 along an inner surface 68 on an opposite side of an outer surface 66. The at least one cable 20 is arranged to slide within the upper and lower guides 32, 34, 38, 40. The plurality of guides is preferably integrally formed with at least one of the respective upper and lower parts 12, 14 upon which they are located, although they may be separate and attached to the upper and lower parts as well. As shown, at least one of the plurality of guides 34 forms a semi-circular shape for redirecting the cable.

Figure 6:
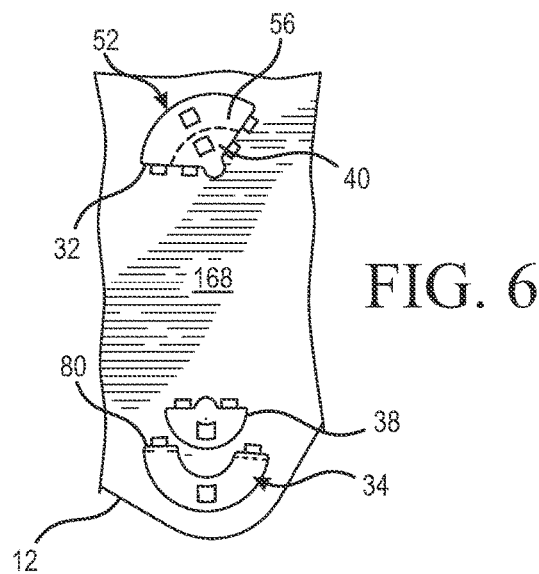
FIG. 6 is a sectional view showing guides located along an inner surface of an upper part in the embodiment of FIG. 2.

In an example shown in FIG. 6, at least one of the plurality of guides 34 forms a channel 80 through which the at least one cable 20 extends. In a variation, also shown in FIG. 6, at least two of the guides 32, 40 may be defined by channels of the guide component 52 separated by a divider 56. Further, when two guides 32, 40 are stacked with one located interiorly the other, they may form different radii.

The lower part 14 forms a guide 36 along an inner surface 70 opposite an outer surface 72. The inner surface 70 of the lower part 14 opposes an inner surface 68 of the upper part 12, such that the at least one cable 20 routes between the inner surfaces 68, 70 of the upper and lower parts 12, 14.

For adjusting the height H among the upper and lower parts 12, 14, and hence the anterior component 10 such as by enlarging the tracheal opening 16 and a distance between the tab 22 and the sternum support 30, the at least one cable 20 includes first and second cable segments 20A, 20B extending through the plurality of guides 32, 34, 36, 38, 40 formed by the upper and lower parts 12, 14 for guiding the cable 20 on first and second sides 74, 76 of the anterior component 10 from a vertical centerline A-A.

First and second ends of the first and second cable segments 20A, 20B are received by the tensioning device 18. The first and second cable segments 20A, 20B are arranged to continuously extend through the plurality of guides 32, 34, 36, 38, 40. The upper part 12 defines at least one retainer 42, 46 for securing the tensioning device 18 thereto. The at least one retainer 46 defines at least one opening 48, 50 for guiding the cable 20 therethrough.

According to adjustment of the tensioning device 18, a length of the first and second cable segments 20A, 20B is reduced such that the cable 20 pulls a lower periphery 78 of the lower part 14 via the guide 36 toward a lower periphery 64 of the upper part 12 to reduce the height H of the anterior component 10. Release of the tensioning device 18 allows for the at least one cable 20 to unspool so the height H of the anterior component 10 can be increased. The tensioning device 18 may be locked once the desired height H of the anterior component 10 is established. Further adjustment in reducing the height H may be achieved by incremental adjustment of the tensioning device 18.

When fitting a cervical collar having an anterior component 10, a clinician fits the mandibular support and posterior component against a patient's chin and head, arranged for the desired level of immobilization and support. The clinician then adjusts the side adjustment mechanism and the tensioning device 18 to secure the anterior component 10 against the chest and shoulders of the patient. A clinician may also first fit the anterior component 10 against the patient's chest and then adjust the side adjustment and the tensioning device 18 to extend the mandibular support and posterior component to the chin and head of the patient. The height setting can then be locked at the desired height setting to ensure a proper fit for the user.

The side height mechanism allows for coarse adjustment of the height between the sides of the upper and lower parts, and the tensioning device and cable allow for finer height adjustment at the tracheal opening, particularly since the center portion of the anterior component inclusive of the tracheal opening is broader when contoured about the user's neck so that the upper and lower parts pivot at the side height mechanism by height adjustment at the center of the anterior component.

An example of the device may be a rotary type device. Exemplary rotary type devices are described in U.S. Pat. No. 5,934,599, granted August 1999; U.S. Pat. No. 6,202,953, granted March 2001; U.S. Pat. No. 6,289,558, granted September 2001; U.S. Pat. No. 7,198,610, granted Apr. 3, 2007; and U.S. Pat. No. 7,992,261, granted Aug. 9, 2011.

Figure 4:
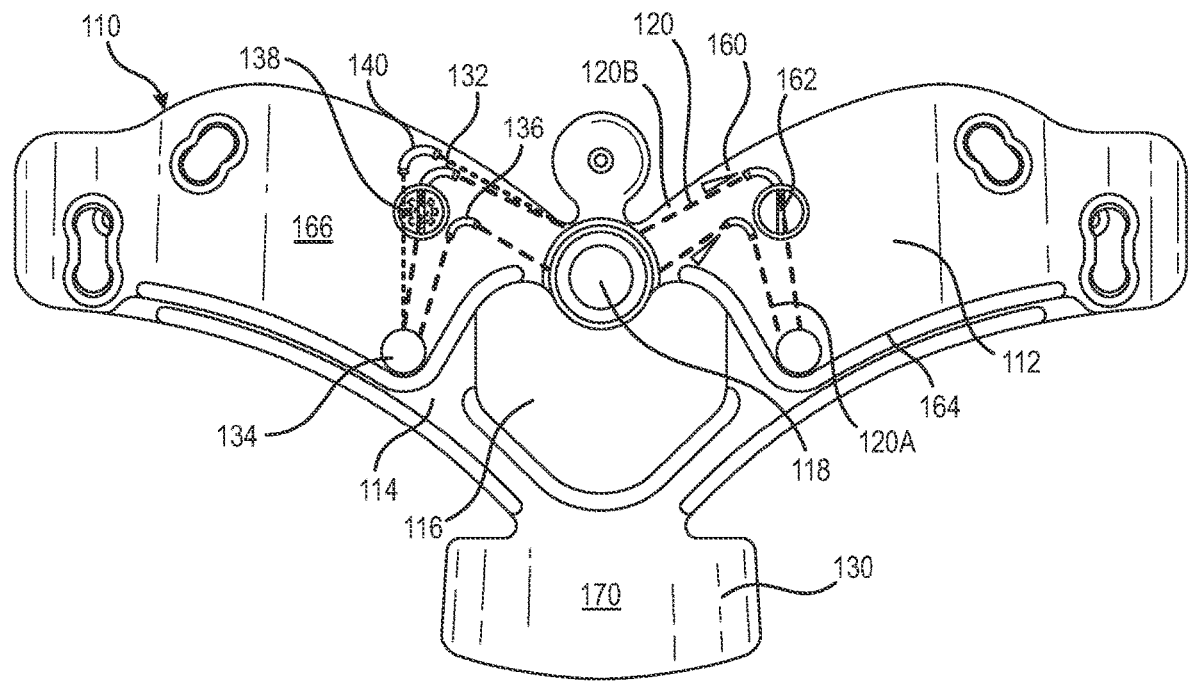
FIG. 4 is a front elevational view showing another embodiment of a cervical collar.
Figure 5:
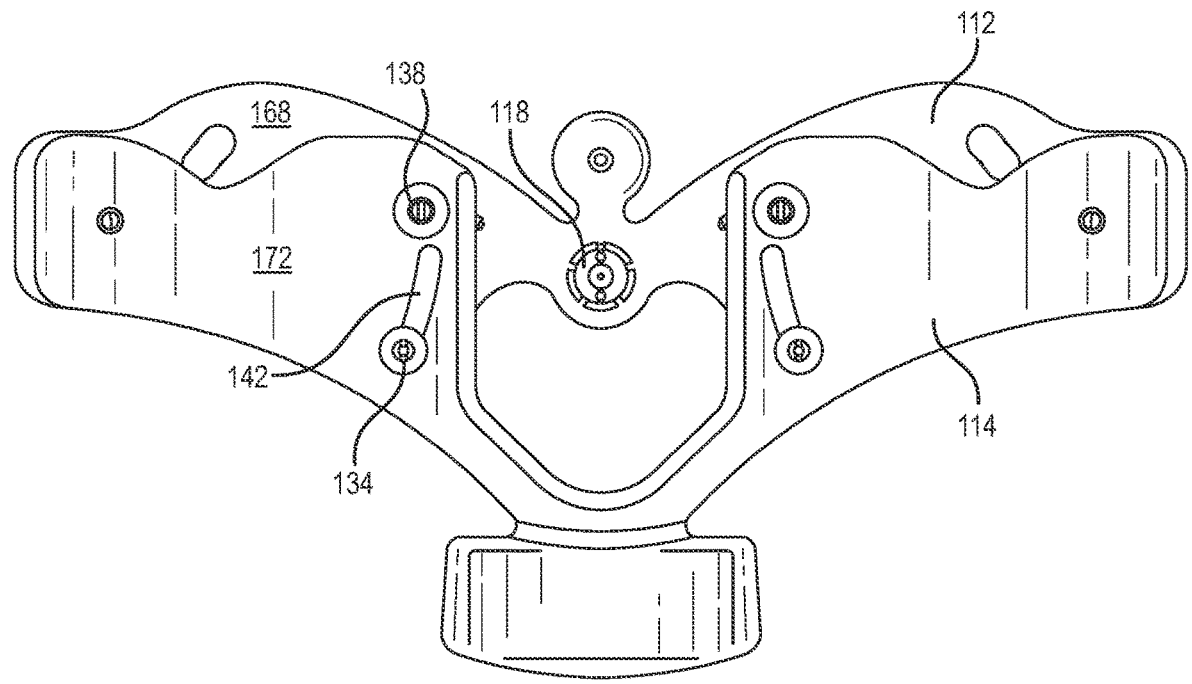
FIG. 5 is a rear elevational view showing the embodiment of FIG. 4.

FIGS. 4 and 5 illustrate another embodiment of an anterior component 110 arranged for height adjustment using an alternative cable configuration with slidable fasteners. The anterior component includes an upper part 112, a lower part 114 connected to the upper part 112, a tensioning device 118, as in the foregoing embodiments, connected to the upper part 112, and at least one cable 120 engaging between the upper and lower parts 112, 114 and arranged to be shortened or lengthened relative to the upper and lower parts 112, 114 by the tensioning device 118 to move the lower part 114 relative to the upper part 112. The tensioning device 118 is mounted on an outer surface 166 of the upper part 112. The anterior component defines a centrally located tracheal opening 116 such that a height of the tracheal opening 116 varies according to a length of the cable 120. The lower part 114 defines a sternal support 130 extending downwardly below and beyond a lower periphery 164 of the upper part 112.

The anterior component 110 includes a plurality of guides 132, 136 formed along an inner surface 168 of the upper part 112 for guiding the cable 120. Each of the first and second sides of the upper part 112 extending from the tracheal opening 116 include a plurality of guides 132, 136 arranged symmetrically with one another. First and second ends of first and second cable segments 120A, 120B of the at least one cable 120 are received by the tensioning device 118, and the first and second cable segments 120A, 120B continuously extend through the plurality of guides 132, 136.

The first cable segment 120A has a first end coupled to the tensioning device 118 and a second end arrested by a cable arrest 138 mounted on the lower part 114. The first cable segment 120A extends from the tensioning device 118 toward and through a first guide 136 located on an inner surface 168 of the upper part 112, then toward and securing to a fastener 134 coupled to the upper part 112 and slidably engaging the lower part 114, and then toward and arrested by a cable arrest 138 secured to the lower part 114.

The fastener 134 slidably engages the lower part 114 along a slot 142 formed by the lower part 114. The slot 142 has a generally arcuate shape to accommodate movement between the upper and lower parts 112, 114. The upper part 112 defines an opening opposite the fastener 134 located on and secured to the lower part 114.

In this embodiment and those that follow, arcuate slots are used for translation between the upper and lower parts. The arcuate slots are arranged to allow for movement between the upper and lower parts in a more anatomically relationship, and thereby provide a spatial relationship between the upper and lower parts that better fits the anatomy of the user.

The upper part 112 preferably defines an upper guide 132 located above the cable arrest 138 through which a second segment 120B of the at least one cable 120 extends and is guided toward the tensioning device 118. The inner surface 168 of the upper part 112 defines a plurality of bosses 160 located proximate the tensioning device 118 for routing the at least one cable 120. The at least one cable 120 extends and is routed about both first and second sides of the upper and lower parts 112, 114 extending from the tracheal opening 116.

Figure 7:
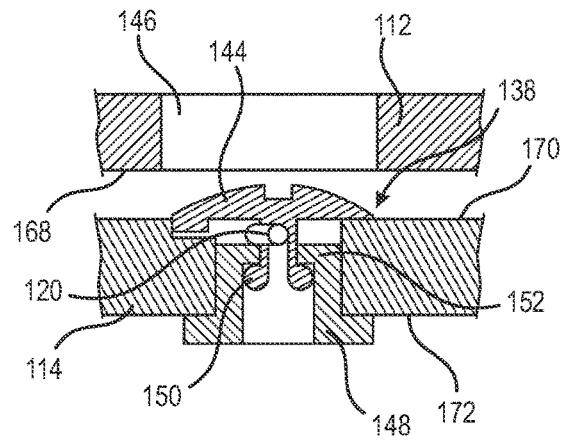
FIG. 7 is a schematic view of a cable arrest in the embodiment of FIGS. 4 and 5.
Figure 8:
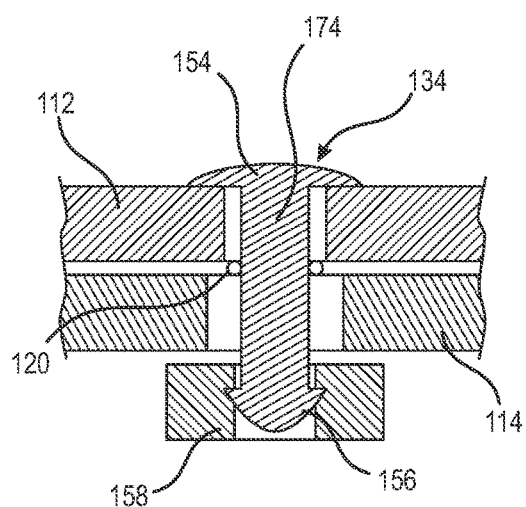
FIG. 8 is a schematic view of a fastener in the embodiment of FIGS. 4 and 5.

As shown in FIGS. 7 and 8, the at least one cable 120 is confined between the inner surfaces 168, 170 of the upper and lower parts 112, 114. The cable arrest 138 extends between inner and outer surfaces 170, 172 of the lower part 114. The cable arrest 138 includes a cap 144 resting on the inner surface 170 of the lower part 114 and has a coupling part 150 arranged to engage with shoulders 152 of a base 148. The base 148 engages the outer surface 172 of the lower part 114.

The cable arrest 138 includes an aperture 162 through which the at least one cable 120 extends. The aperture 162 holds the at least one cable 120 and prevents movement of a portion of the at least one cable 120 extending through the aperture 162. The fastener 134 has a top 154 engaging the outer surface 166 of the upper part 112. A shaft 174 extends through thicknesses of the upper and lower parts 112, 114. A bottom 156 is held by a retainer 158 engaging the outer surface 172 of the lower part 114. The at least one cable 120 slidably extends about the shaft 174 between the inner surfaces 168, 170 of the upper and lower parts 112, 114. The anterior component 110 connects to a mandibular support and posterior component according to the Miami J collar or another support component and functions similarly to the anterior component 10 of the embodiment of FIGS. 2 and 3.

Figure 9:
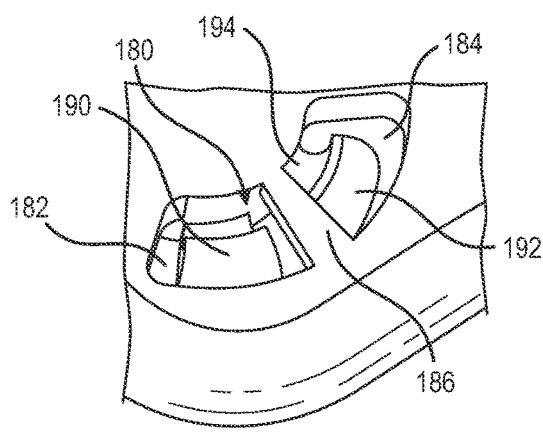
FIG. 9 is a front schematic view of another embodiment of a guide.
Figure 10:
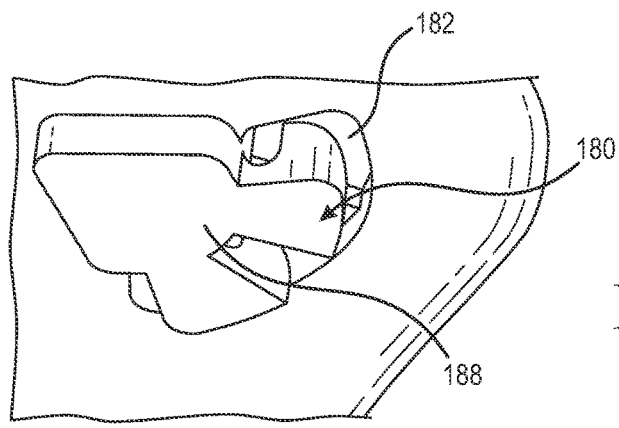
FIG. 10 is a rear schematic view of the guide of FIG. 9.

FIGS. 9 and 10 show a variation of a guide 180 formed by first and second openings 182, 184 separated by a divider 186, and defined by one of the upper and lower parts to an anterior component, such as those in FIGS. 2-5. A retainer 188 is attached or formed by the upper and lower parts and defines first and second prongs 190, 192 that define a channel 194 for receiving a cable therein. The prongs 190, 192 retain the cable within the channel 194, and the prongs may each be arranged for guiding the cable in a predetermined direction to facilitate height adjustment of the anterior component.

Figure 11:
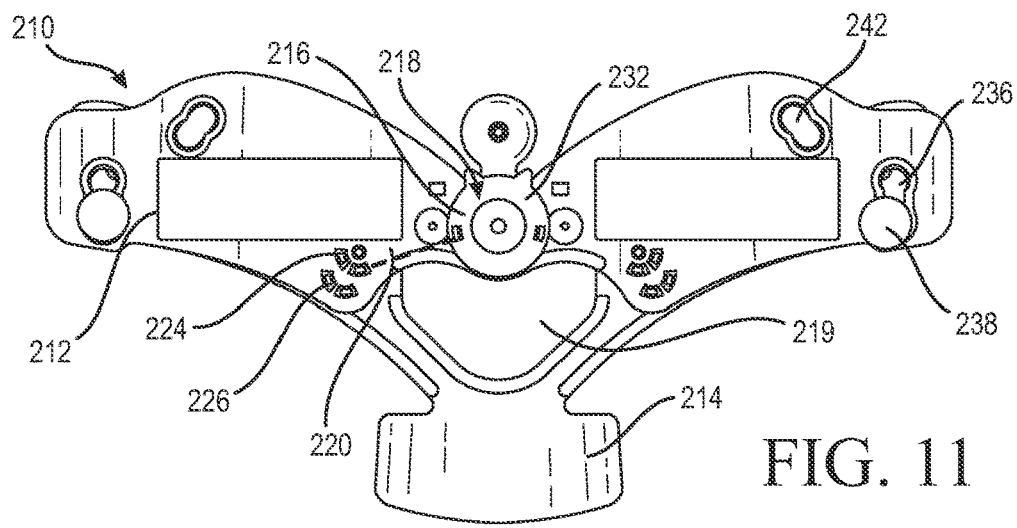
FIG. 11 is a front elevational view showing another embodiment of a cervical collar.
Figure 12:
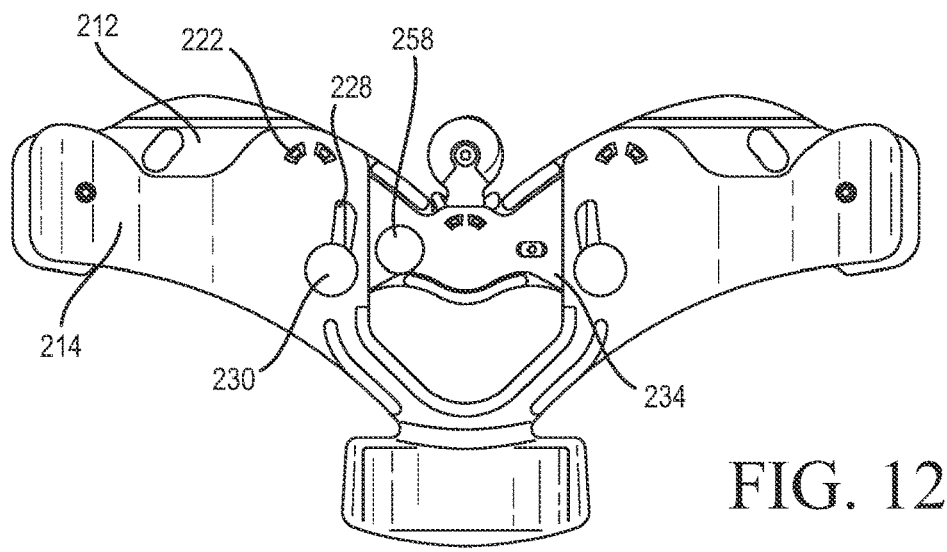
FIG. 12 is a rear elevational view showing the embodiment of FIG. 11.

FIGS. 11 and 12 exemplify yet another embodiment of an anterior component 210 having upper and lower parts 212, 214 adjustable relative to one another for modifying the height of the anterior component 210, as with previous embodiments the anterior component is configured for receiving a mandibular support and posterior component similar to the Miami J collar. In this embodiment, the tensioning device 218 includes a lock 216 that prevents a user from tampering or inadvertently adjusting the tensioning device 218 so a clinician can set the height of the anterior component.

The tensioning device 218 includes a cable 220 (schematically shown) and operates similarly to the preceding embodiments. This embodiment, however, has a different pattern of guides in that the cable 220 extends through an outer lower guide 226 on the upper part 212 to an upper guide 222 on the lower part 214, to an upper lower guide 224 on the upper part 212, for adjusting the height of the anterior component 210. The lower part 214 defines arcuate slots 228 on opposed sides of the tracheal opening, and a pair of pins 230 secure to the upper part 212 and extend through the arcuate slots 228, as shown in FIG. 12. As with the preceding embodiments, the upper part 212 defines a side adjustment connection 242 for receiving the mandibular support.

Figure 13:
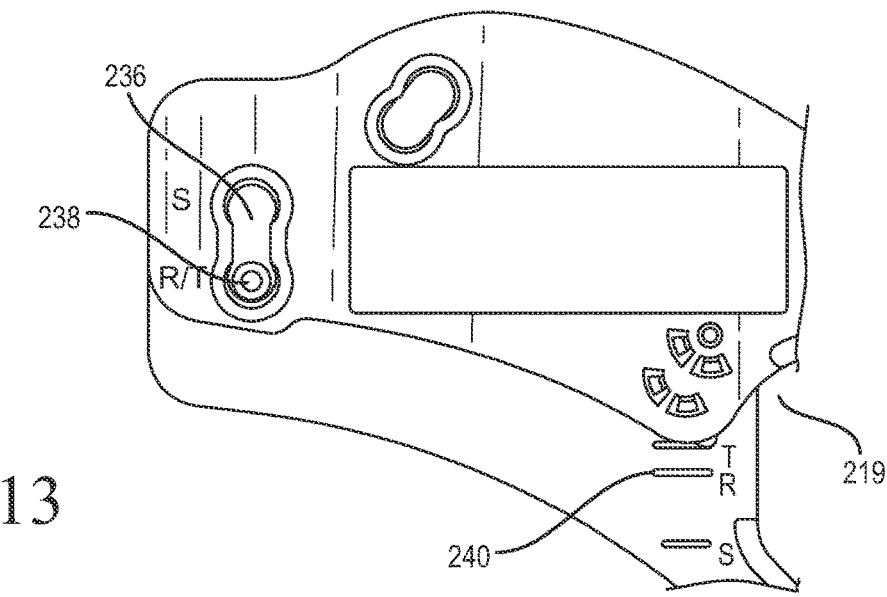
FIG. 13 is a front schematic view showing rear adjustment relative to front adjustment of the anterior component.

FIG. 13 shows a side height mechanism including a female component 236 having at least two side height settings, for example small and regular/tall. The female component receives the fastener 238 used for selecting the side heights. The lower part 214 includes indicia 240 along the tracheal opening 219 for showing the height at the center of the anterior component 210, which may be different from the height at the side height settings in the event a greater center height is required for an individual user.

Figure 14:
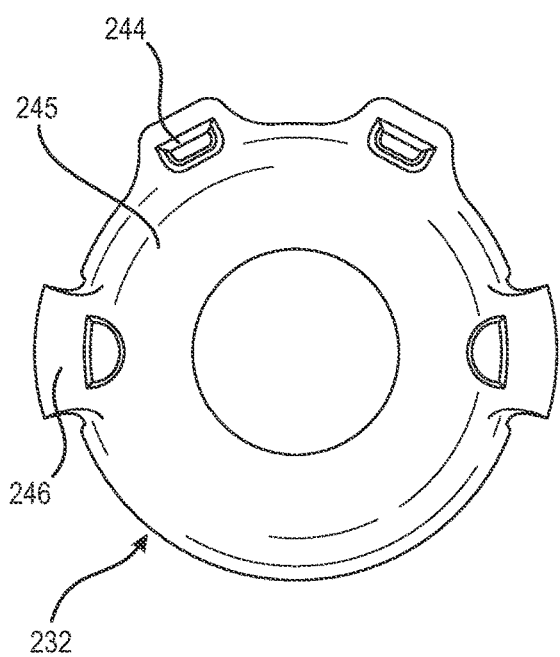
FIG. 14 is a front elevational view of a front lock for an adjustment device.
Figure 15:
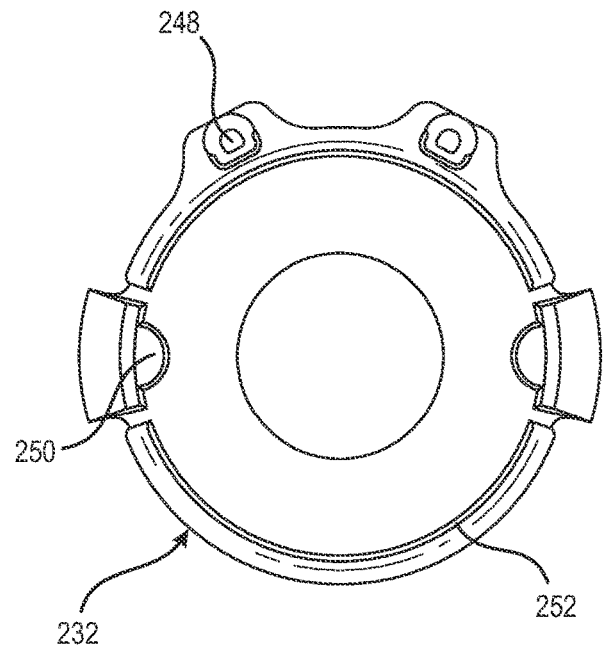
FIG. 15 is a rear elevational view of the lock of FIG. 14.
Figure 16:
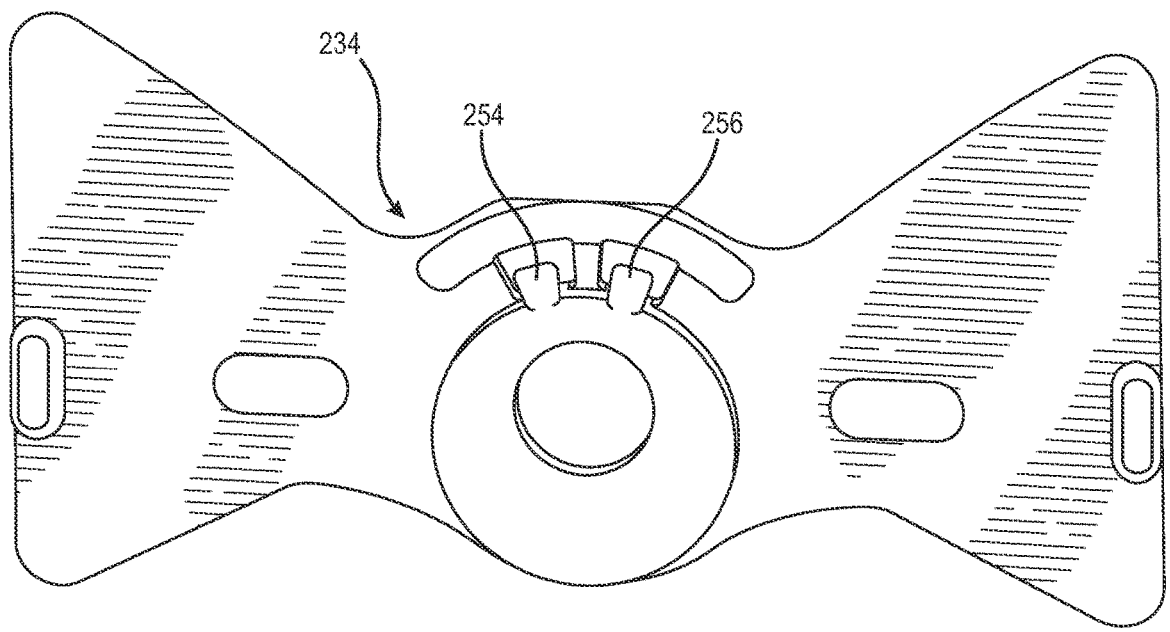
FIG. 16 is a perspective view of a rear lock for an adjustment device in combination with the front lock of FIG. 14.

FIGS. 14-16 show detailed views of components of the lock 216. Specifically, FIGS. 14 and 15 show a lock cover 232 having a plate 245 with flanges 244, 246 for carrying prongs 248, 250 adapted for securing over a dial of a tensioning device. A rim 252 may protrude from the rear side of the plate 245 so as to secure about a periphery of the tensioning device, as shown in FIG. 11.

FIG. 16 shows a rear lock plate 234 that is adapted for securing against and being received by the upper part 212, and retained thereon by a fastener 258, as shown in FIG. 12. The rear lock plate 234 has tabs 254, 256 which can mate with the prongs 244 of the lock cover 232 for securing the lock cover 232 to the rear lock plate 234, and thereby the anterior component 210.

Figure 17:
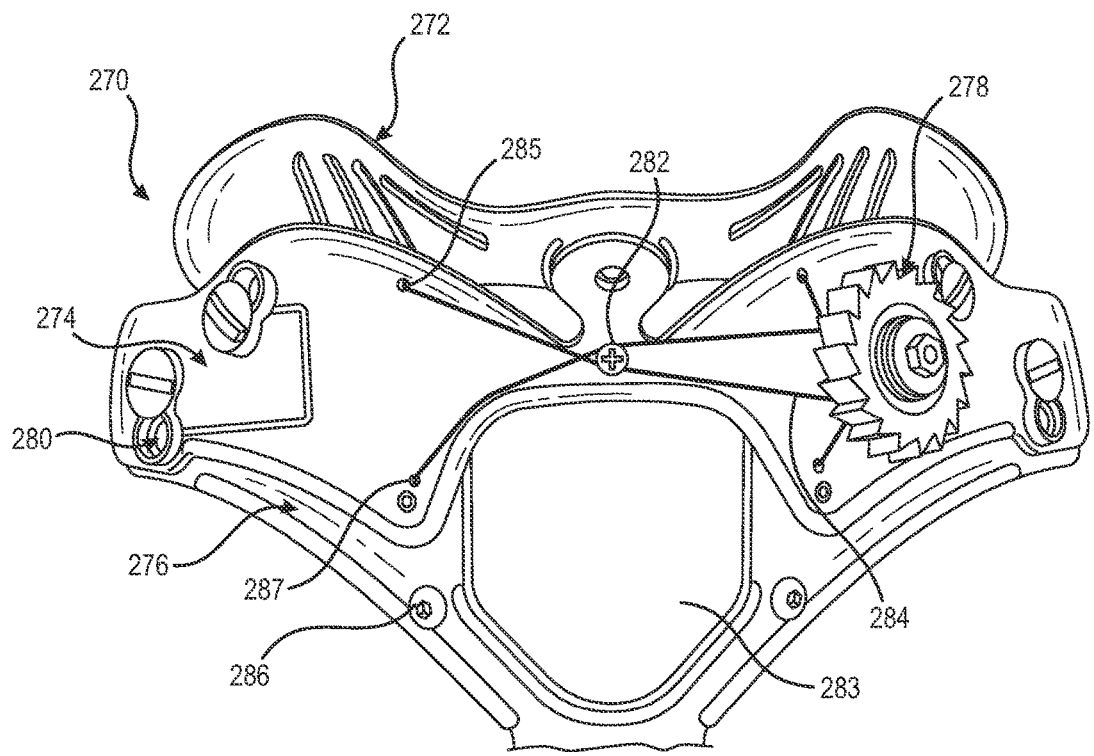
FIG. 17 is a front elevational view showing another embodiment of a cervical collar.
Figure 18:
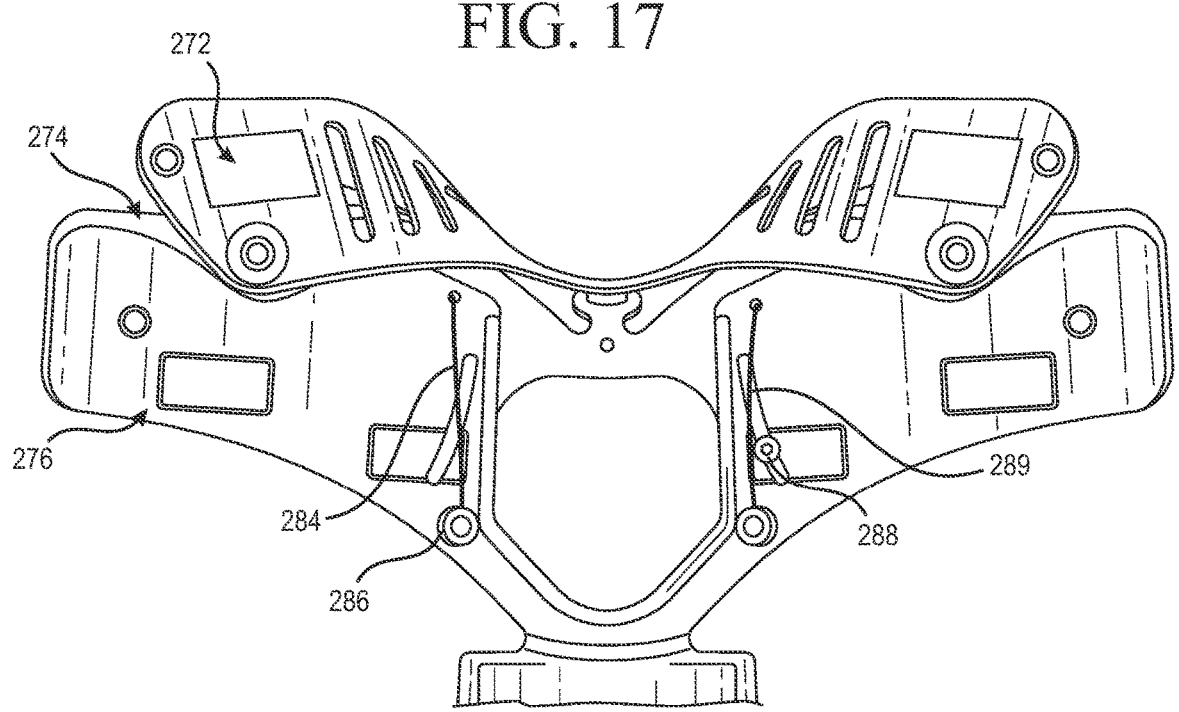
FIG. 18 is a rear elevational view showing the embodiment of FIG. 17.

FIGS. 17 and 18 depict another embodiment of an anterior component 270 that allows height adjustment without modifying the central portion of the anterior component 270. The anterior component 270 is shown with a mandibular support 272 of the type in the Miami J attached to an upper part 274 that is adjustably connected to a lower part 276. A tensioning device 278 is located at a side of the upper part 274, and a side height mechanism 280, as in preceding embodiments, secures the sides of the upper and lower parts 274, 276 to one another. A cable 284 extends from the tensioning device 278 and extends about a central guide 282 on the upper part 274 for routing the cable 280 to openings 285, 287 defined by the upper part 274.

Ends of a first segment of the cable 284 are received by anchors 286 corresponding to opposed sides of the tracheal opening 283, and rotation of the tensioning device 278 operates the cable 284 similarly to preceding embodiments. Upon movement of the upper part 274 relative to the lower part 276, a pin 288 held by the upper part 274 and upon which ends of a second segment of the cable 284 are secured and the pin 288 slides within a slot 289 formed by the lower part 276 to maintain relative movement of the upper part 274 relative to the lower part 276.

An advantage of this embodiment is that the tensioning device may be mounted on a side of the upper part 274 so the central portion of the anterior component requires no modification. The tensioning device 278 can have segments of the cable extend to the other side of the upper part and couple with the pin and anchor for such side, while having a similar configuration on the side upon which it secures.

Figure 19:
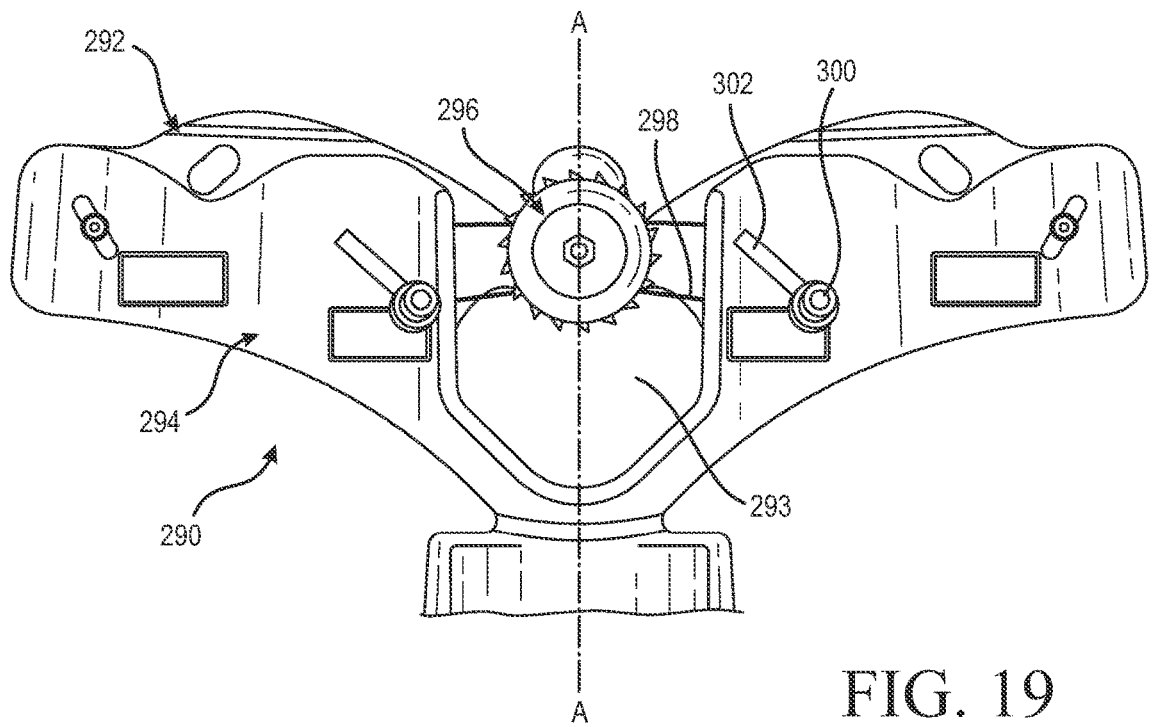
FIG. 19 is a front elevational view showing another embodiment of a cervical collar.
Figure 20:
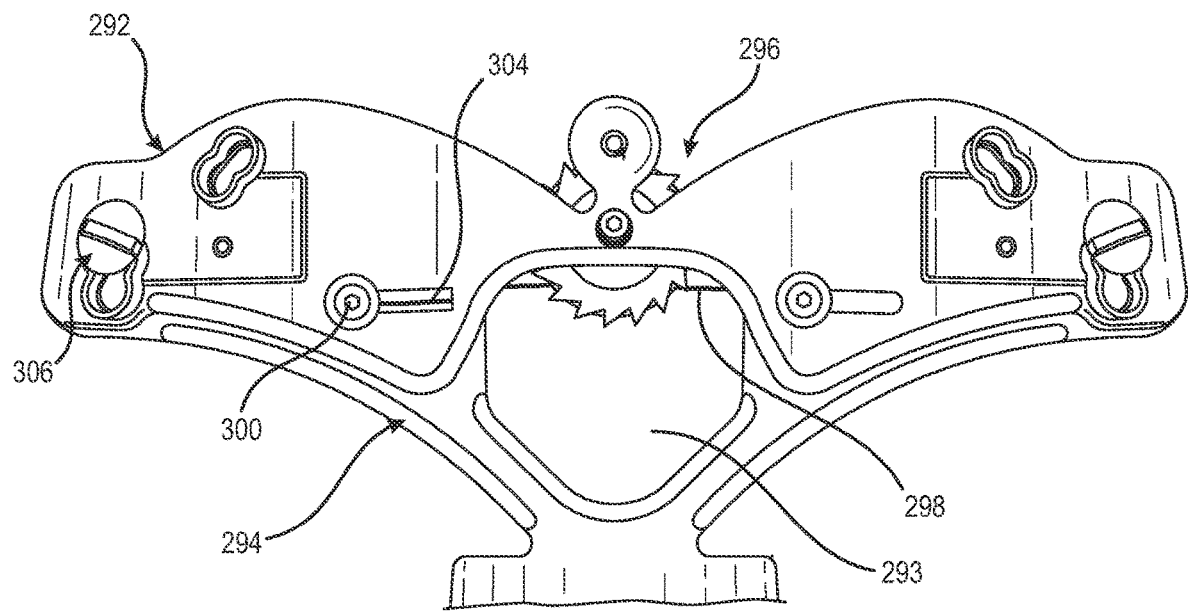
FIG. 20 is a rear elevational view showing the embodiment of FIG. 19.

FIGS. 19 and 20 exemplify another embodiment of an anterior component, configured to use a pin and slot system for movement of the upper and lower parts 292, 294. In this embodiment, the anterior component 290 has upper and lower parts 292, 294 as in other embodiments, and are adjustable at the side ends by side height mechanisms 306. A dial tensioning device 296 is centrally located, as in some of the foregoing embodiments, and a cable 298 has segments extending to pins 300 on opposed sides of the tracheal opening 293. Although not shown, guides may be formed to route segments of the cable 298 between the upper and lower parts 292, 294. The pins 300 are arranged to slide between slanted or oblique slots 302 relative to the vertical center line A-A, and formed by the lower part 294. The pins 300 likewise slide within lateral or horizontal slots 304 relative to the vertical center line A-A, and formed by the upper part 292. Adjustment of the tensioning device 296 causes relative movement of the upper and lower parts 292, 294 as a results of the pins 300 sliding within the slots 302, 304.

Figure 21:
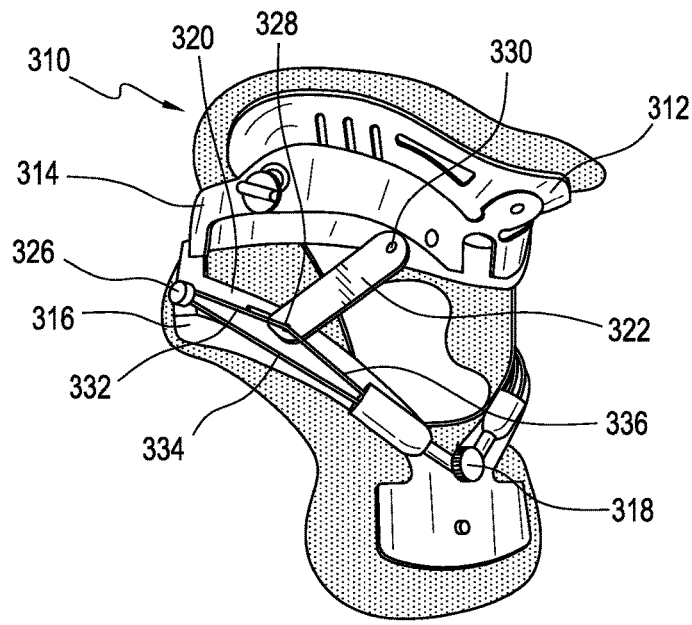
FIG. 21 is a perspective view of another embodiment of a cervical collar.
Figure 22:
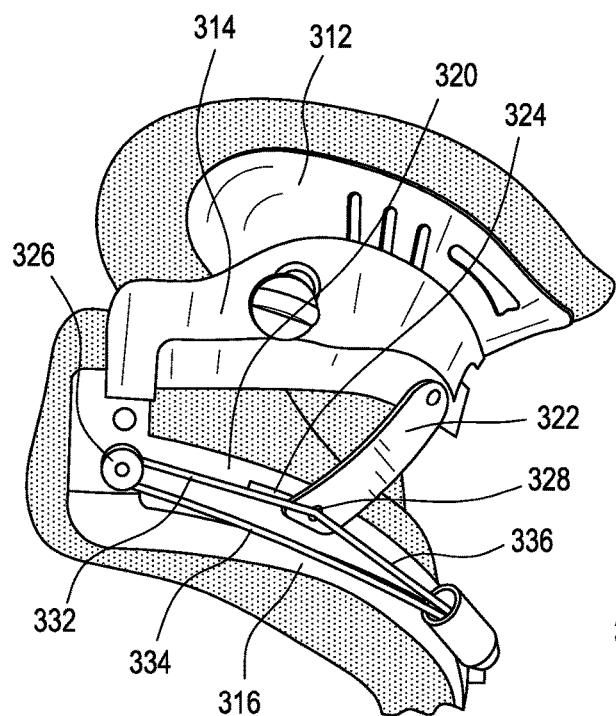
FIG. 22 is a side elevational view of the embodiment of FIG. 21 in an elevated configuration.
Figure 23:
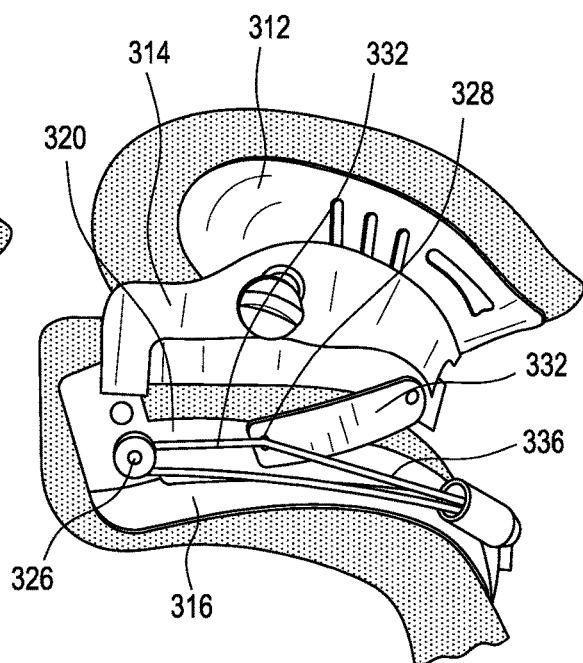
FIG. 23 is a side elevational view of the embodiment of FIG. 21 in a retracted configuration.

FIGS. 21-23 depict another anterior component 310 having height adjustment among upper and lower parts 314, 316, in which the mandibular support 312 secures to the upper part 314 in the same manner as the Miami J and possesses the same contours. The anterior component 310 includes a dial 318 located on the lower part 316, although it can be rearranged to the upper part 314, that adjusts a link system connecting the upper and lower parts 314, 316.

The link system includes a bottom link 320 having a first end connecting to a pivot connection 326 at a side connection of the upper and lower parts 314, 316 and near the vertical center line of the anterior component on the lower part 314. A top link 322 connects to the bottom link 320 along a slot 324 via a pin or connection 328 and pivotally connects to the upper part 314 at a connection 330. An actuator 340 connects to the dial 318 and has a rear linkage portion 332 engaging the pivot connection 326 and connecting to the pin 328, a front linkage portion 336 connecting to the dial 318 and the pin 328, and a lower linkage portion 334 connecting to the pivot connection 326 and the dial 318.

The rear linkage portion 332, and the lower linkage portion 334, the front linkage portion 336 may define a continuous belt that is biased about the pivot connection 326, the pin 328 and the dial 318, so that it can be continuously adjusted. The dial may include a screw or worm gear or other suitable actuator that enables adjustment of the belt to allow it to adjust so as to increase or decrease the anterior component height.

Figure 24:
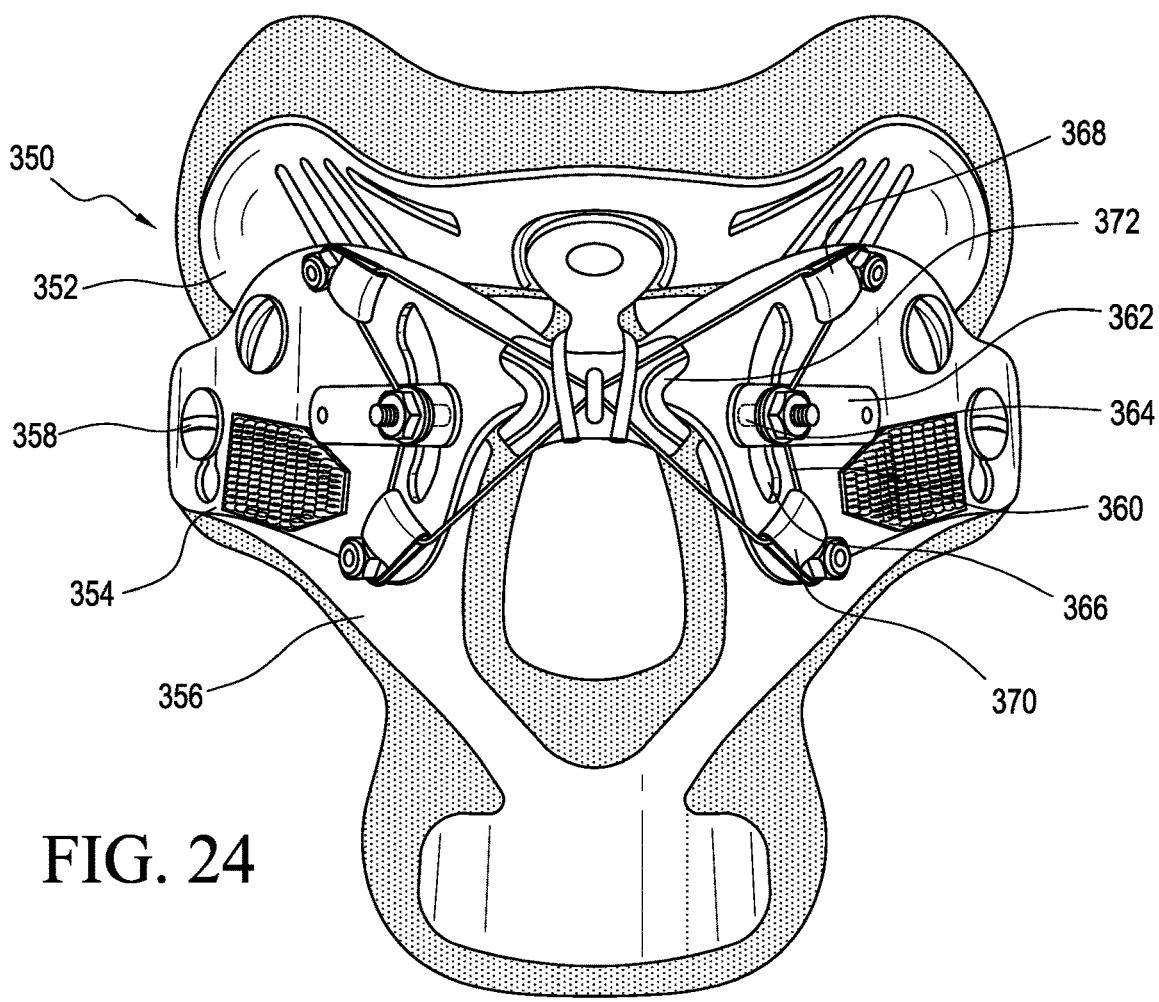
FIG. 24 is a front elevational view showing another embodiment of a cervical collar.

FIG. 24 illustrates another anterior component embodiment 350 having height adjustment among upper and lower parts 354, 356 with a pin and lever actuating system, in which the mandibular support 352 secures to the upper part 354 in the same manner as the Miami J and possesses the same contours. A side height mechanism 358 connects the sides of the upper and lower parts 354, 356, as in other embodiments. A cable 360 is routed about guides 368, 370 to a bolster 372 that is centrally located arranged on the anterior component so that the cable 360 routes along or through formed thereon, such that the cable may form an "X" along the bolster. The bolster 372 is secured mounted on the anterior component. A lever 362 is pivotally mounted on the upper part 354 and a pin 364 is located on an end portion thereof for slidably extending through a slot 366 formed by the upper part 354. The pin 364 is secured to the lower part 356, and upon movement of the lever 362, the bolster 372 resists movement of the cable and maintains the lever in place upon movement by a user for adjustment in height of the lower part 356 relative to the upper part 354.

The bolster 372 preferably is unmovable whereas the cable length remains the same but its length varies between the guides and the bolster according to movement of the lever, with the bolster resisting the cable. Because of the bolster 372, adjustment of a first lever on a first side of the anterior component causes the second lever on the second side to adjust commensurate with the first lever because of the cable length does not adjust.

Figure 25:
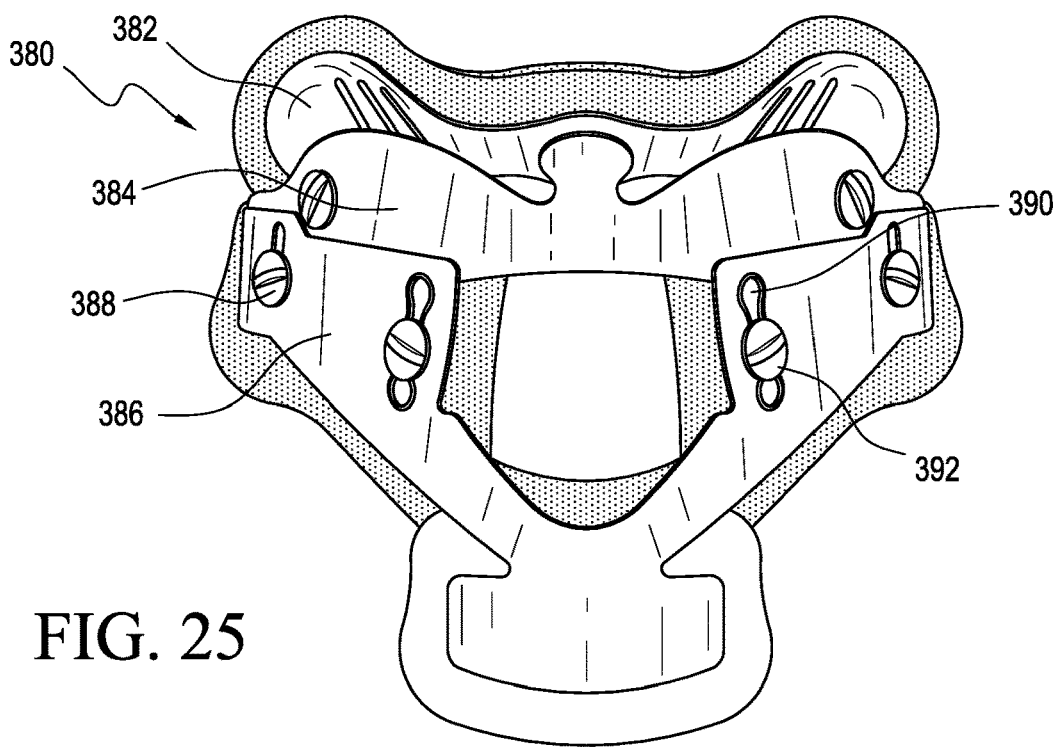
FIG. 25 is a front elevational view showing another embodiment of a cervical collar.

FIG. 25 depicts another anterior component embodiment 380 having height adjustment among upper and lower parts 384, 386 using only female components and fastener units, in which the mandibular support 382 secures to the upper part 384 in the same manner as the Miami J and possesses the same contours. A side height mechanism 388 connects the sides of the upper and lower parts 384, 386, as in other embodiments. A central height adjustment is provided resembling the side height mechanism 388, and includes a plurality of female components 390 formed by the lower part 386, and defining a plurality of height settings, preferably more than the side height mechanism 388. The female components, as with other embodiments, defines sequential larger opening along a slot, as depicted in FIG. 25. A fastener unit 392 is providing for locking in place among one of the plurality of height settings and engaging a receptacle (not shown) of the upper part 384, for maintaining a height relationship between the upper and lower parts 384, 386.

Figure 26:
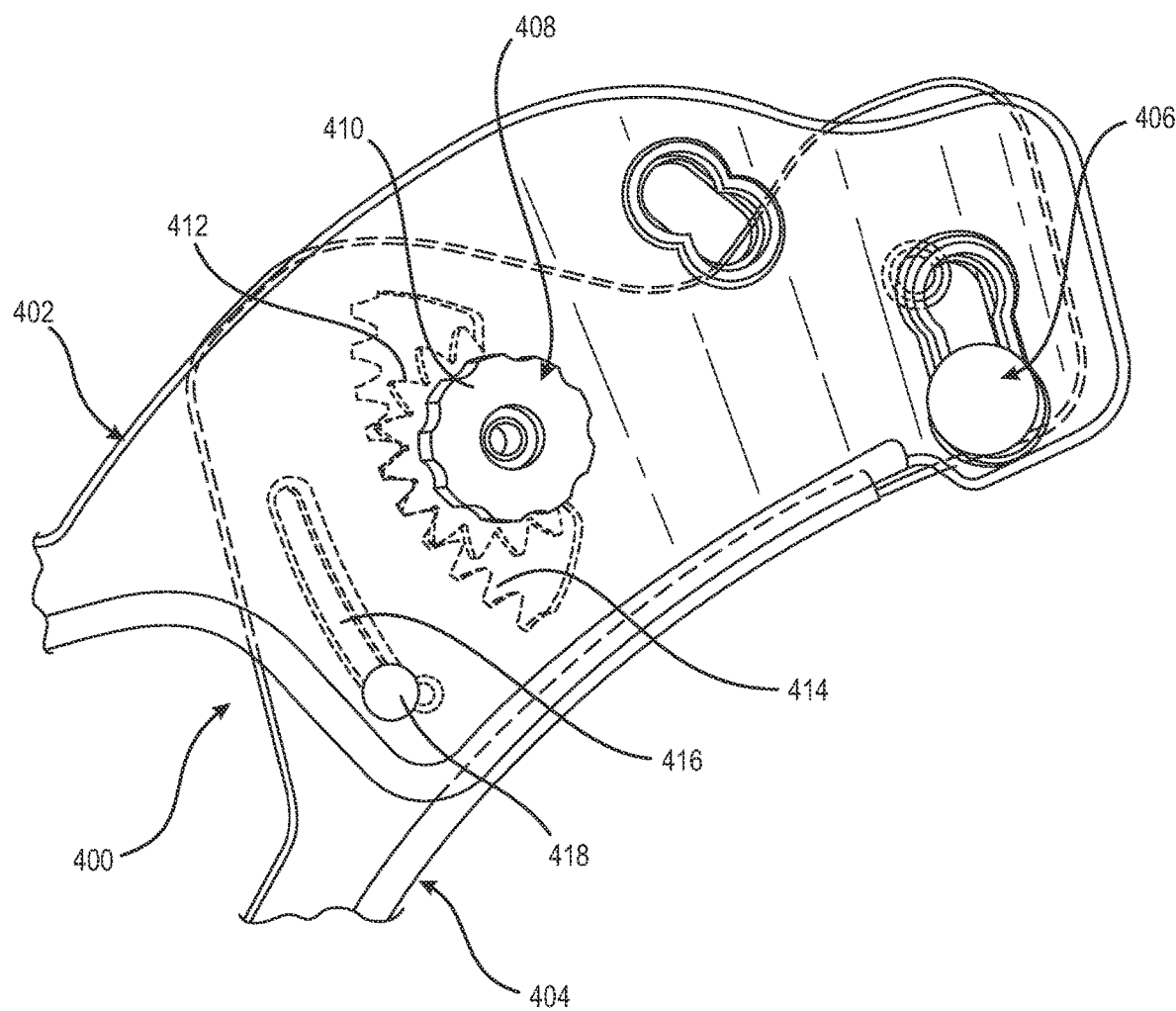
FIG. 26 is a sectional view showing another adjustment system in a cervical collar.

FIG. 26 shows a schematic view of another mechanism 400 for an anterior component using a rack and pinion system, in which the mandibular support secures to the upper part in the same manner as the Miami J and possesses the same contours. Upper and lower parts 402, 404 are provided and a side height mechanism 406 is used as in preceding embodiments. A dial mechanism 408 is provided on opposed sides of the upper and lower parts 402, 404. The dial mechanism 408 may be rotatably connected to the upper part 402, and the lower part 404 defines a rack 414 into which a pinion 412 of the dial mechanism 408 engages for adjusting the height between the upper and lower parts 402, 404. A follower pin 418 secured to the lower part 404 slidably engages a slot 416 formed by the upper part 402.

Figure 27:
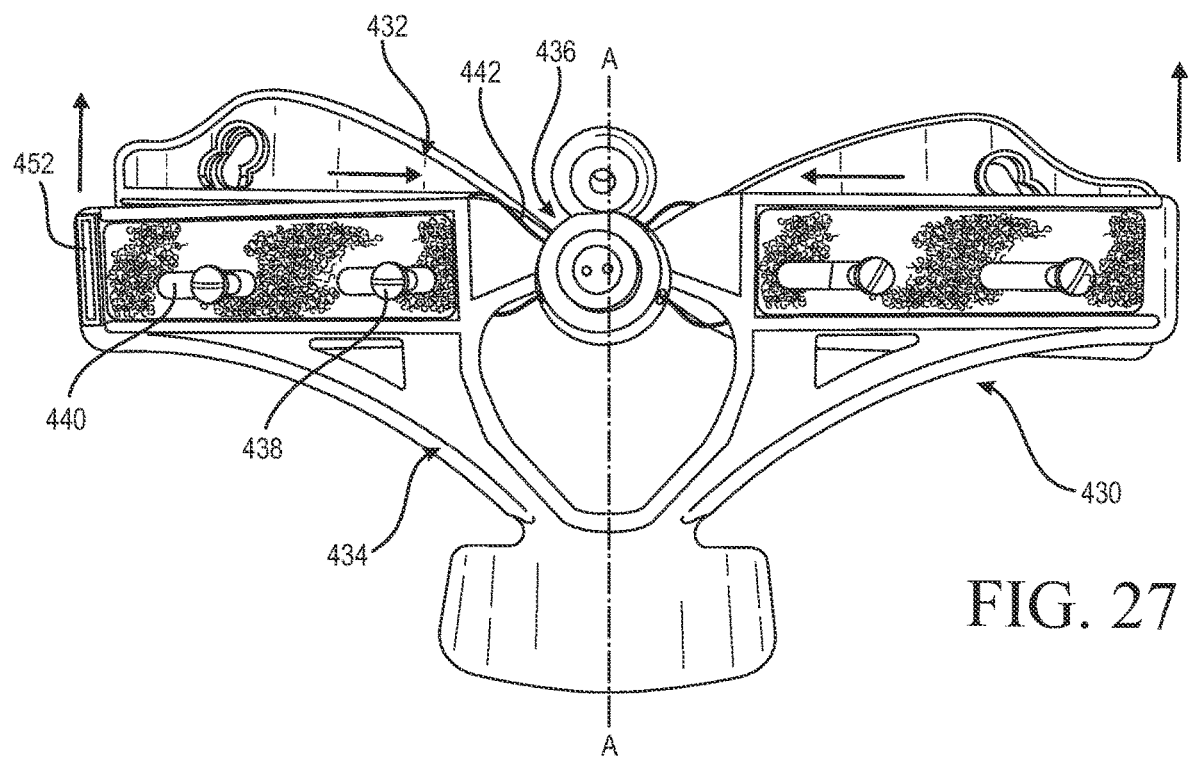
FIG. 27 is a front elevational view showing another embodiment of a cervical collar.
Figure 28:
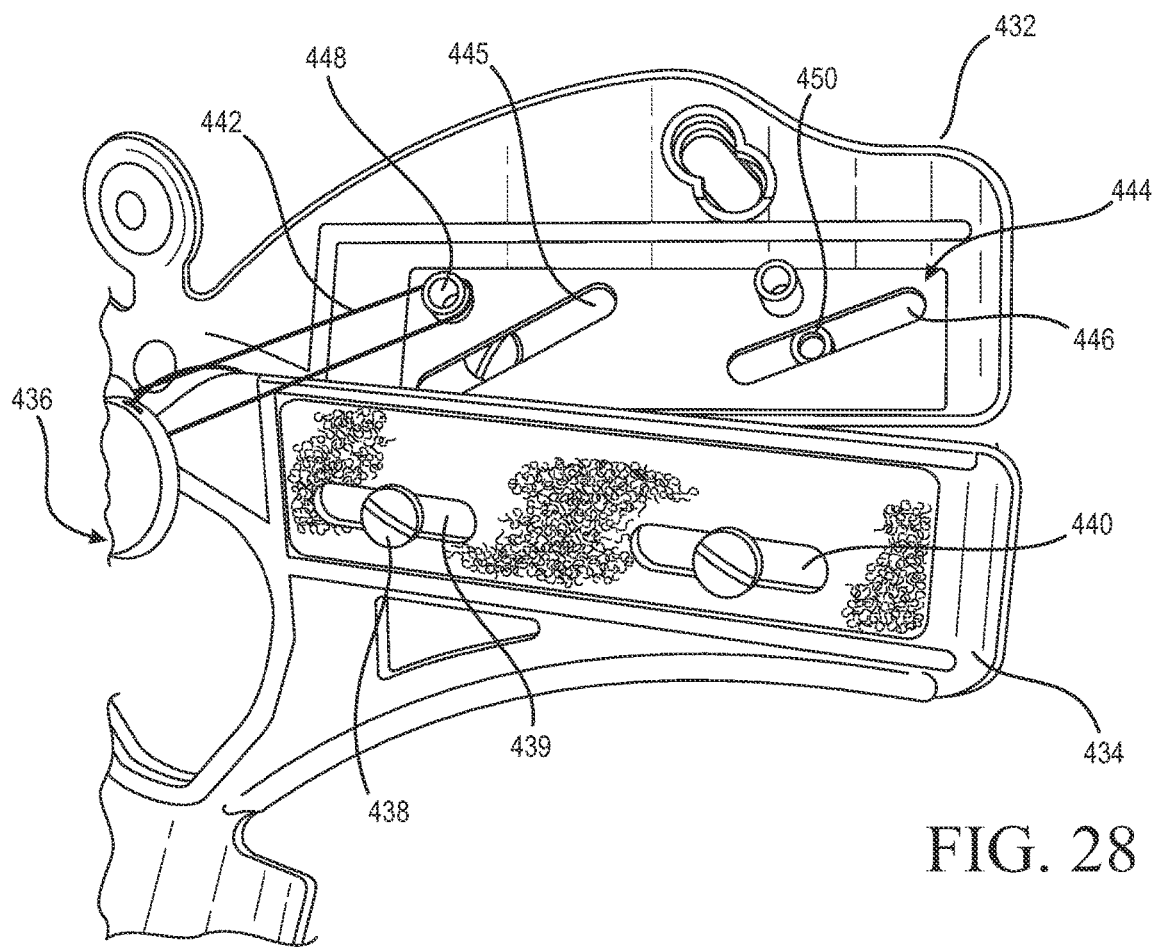
FIG. 28 is a schematic view showing the adjustment system of the embodiment of FIG. 27.

FIGS. 27 and 28 illustrate another anterior component embodiment 430 with slots arranged at multiple angles, in which the mandibular support secures to the upper part in the same manner as the Miami J and possesses the same contours. In this embodiment, upper and lower parts 432, 434 slide in height relative to one another as a result of adjustment of the tensioning device 436. The tensioning device 436 engages a cable 442 that secures about a boss 448 on an intermediate part 444 which slides between the upper and lower parts 432, 434. The intermediate part 444 defines an inner slot 445 arranged at a first angle relative to the vertical center line A-A, and an outer slot 446 arranged at a second angle relative to the vertical center line A-A. The first angle may be steeper relative to the second angle so that the center portion of the anterior component has a height change that is roughly 3:1 the height change at side ends 452, 454 of the anterior component.

The lower part 434 defines first and second slots 439, 440 that are arranged generally horizontally or laterally relative to the vertical center line A-A. Fasteners or pins 438 extend through each of the first and second slots 439, 440, and the corresponding inner and outer slots 445, 446, and engage receptacles 450 on the upper part 432. It follows that upon adjustment of the tensioning device 436, the cable 442 pulls the intermediate part between the upper and lower parts 432, 434, whereby the fasteners 438 slide along the first and second slots 439, 440, and the inner and outer slots 445, 446, to adjust the height of the anterior component 430. The cable 442 can be routed in a reverse manner or likewise routed so that the cable is arranged to increase or decrease the height of the anterior component. For example, the cable can attach to one end of the knob to another end of the intermediate part to move the intermediate part up and down.

Figure 29:
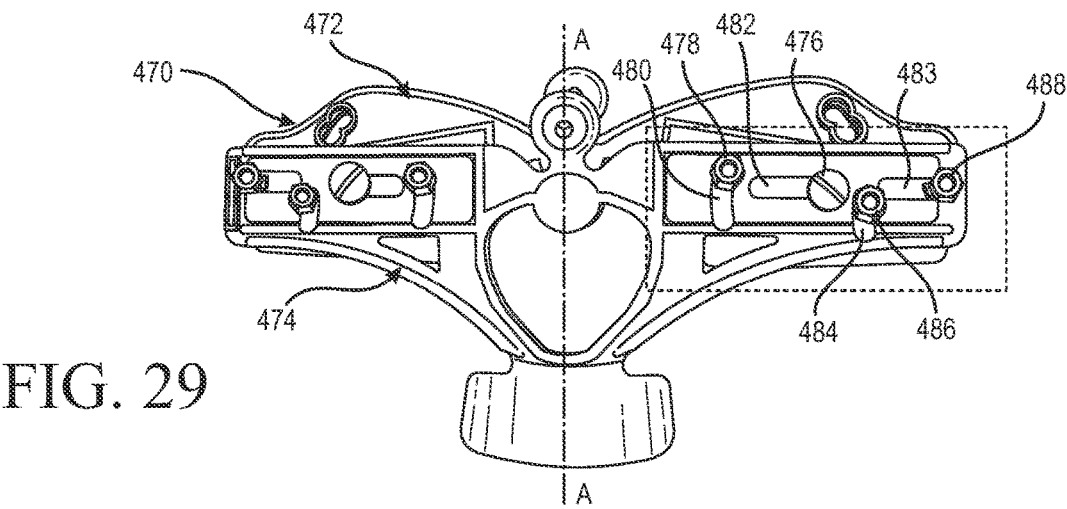
FIG. 29 is a front elevational view showing a cervical collar embodiment which is a variation of the embodiment of FIG. 27.

FIG. 29 shows another anterior component embodiment 470 as a variation of the embodiment of FIGS. 27 and 28 with additional slots, whereby the anterior component 470 has upper and lower parts 472, 474. Opposed sides of the upper and lower parts 472, 474 have generally the same configuration. The lower part 474 defines a first angled slot 480 through which a first fastener or pin 478 extends to secure to the upper part 472, and a second angled slot 484 through which a second fastener 486 extends to secure to the upper part 472. The first and second angled slots 480, 484 may be arranged differently relative to one another, and angled relative to the vertical center line A-A, to obtain height differences of the center portion of the anterior component relative to the side portions.

The lower part 474 also defines first and second horizontal or lateral slots 482, 483, into which third and fourth fasteners 476, 488 extend, respectively, and secure to the upper part 472. The lower part 474 may be adjusted relative to upper part 472 by manually moving the lower part 474 relative to upper part 472, and locking the fasteners against the lower part 474, or alternatively, the anterior component 470 may include a tensioning device as in the embodiment of FIGS. 27 and 28 for adjusting the upper and lower parts relative to one another by a cable and intermediate part arrangement.

Figure 30:
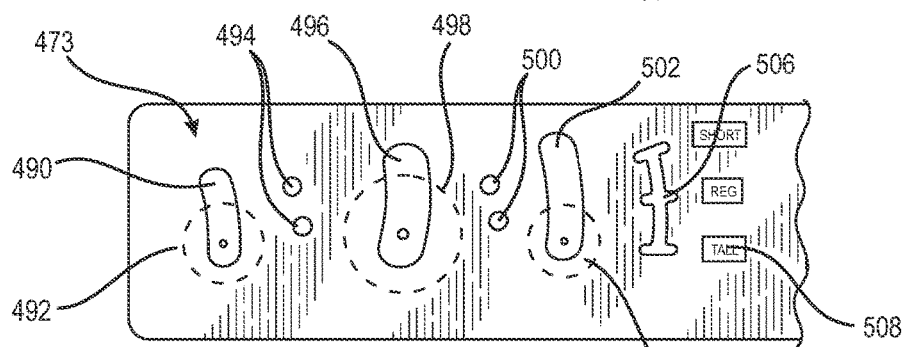
FIG. 30 is a schematic sectional view of a rear part of the cervical collar in FIG. 29.
Figure 31:
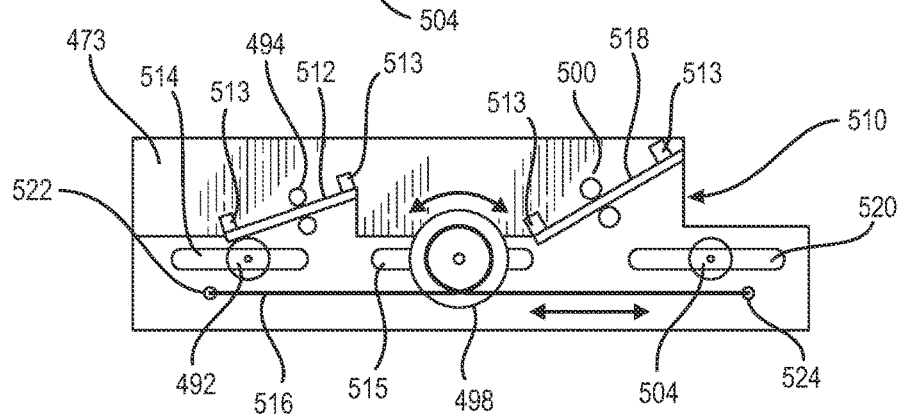
FIG. 31 is a schematic sectional view of an intermediate part of the cervical collar of FIG. 29.
Figure 32:
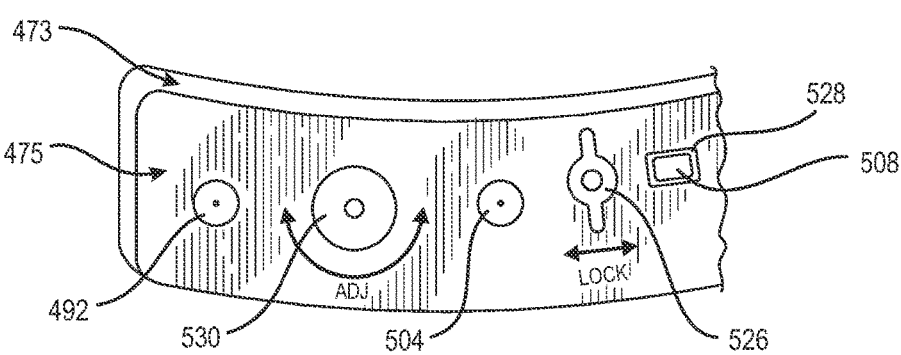
FIG. 32 is a schematic sectional view of a front part of the cervical collar in FIG. 30.

FIGS. 30-32 schematically show a variation of the embodiments of FIGS. 27-29 with different slot and fastener configurations. The upper part 473 defines first, second and third vertical or angled slots 490, 496, 502 relative to the vertical center line. The first, second and third slots 490, 496, 502 may also define an arcuate shape. First and second pin sets 494, 500 extend between the first, second and third slots 490, 496, 502. The upper part 473 includes a side height mechanism including a series of height registers formed by interconnected female components 506, with indicia alongside for showing height settings.

Referring to FIG. 31, an intermediate part 510 is slidable between the upper and lower parts 473, 475. The intermediate part 510 defines first and third horizontal or lateral slots 514, 520 spaced apart by a second horizontal or lateral slot 515. The intermediate part 510 defines inner and outer ramps 512, 518 which bias against the pins 494, 502 as the intermediate part 510 slides relative to the upper part 473. The intermediate part 510 may define bars 513 along each of the inner and outer ramps 512, 518 to control movement of the intermediate part 510 relative to the upper part 473. A tensioning device 530 has a spool 498 that can wind or travel along a cable 516. The cable is preferably anchored at first and second ends 522, 524 to the intermediate part 510. The spool 498 is arranged to slide relative or about the second horizontal slot 515 according to adjustment of the tensioning device 530.

FIG. 32 shows a first pin 492 securing to the lower part 475 and extending through the first slot 490 and the first horizontal slot 514, and a second pin 504 securing to the lower part 475 and extending through the third slot 502 and the third horizontal slot 520. The tensioning device 530, such as a dial tensioning device, is accessible along the lower part 475 and engages the spool 498 for winding or unwinding the cable 516. A fastener component 526 is likewise accessible from the lower part 475 for engaging the female component 506 according to a desired height setting, which is represented through a window 528 formed by the lower part 475 which reveals the indicia 508.

Each of the foregoing embodiments is arranged to receive the mandibular support and posterior component of the Miami J collar, or another cervical collar, while still retaining the clinically recognized superior immobilization and comfort provided by the existing collars. The use of any of the foregoing embodiments with the mandibular support and posterior component of the Miami J collar, or another cervical collar, eliminates the need for pre-sizing and facilitates the fitting of a cervical collar to a patient by a clinician.

While the foregoing embodiments have been described and shown, alternatives, reversal of parts, and modifications of these embodiments, such as those suggested by others may be made to fall within the scope of the invention. Reference characters are provided in the claims for explanatory purposes only and are not intended to limit the scope of the claims or restrict each claim limitation to the element shown in the drawings and identified by the reference character.

The invention claimed is:

1. A cervical collar including an anterior component for coupling to a posterior component having an anatomical contour to circumferentially surround a neck, and a mandibular support having an anatomical contour and coupling to the anterior component, the anterior component defining a vertical centerline, the anterior component comprising:
an upper part arranged for receiving the mandibular support;
a lower part connected to the upper part;
a tensioning device connected to the upper part and arranged on the vertical centerline, wherein the tensioning device is mounted on an outer surface of the upper part, wherein the tensioning device is rotatable around an axis perpendicular to and intersecting the vertical centerline;
at least one cable engaging between the upper and lower parts and arranged to be shortened or lengthened for height adjustment relative to the upper and lower parts by the tensioning device to move the lower part relative to the upper part;
wherein the height adjustment of the upper part relative to the lower part maintains connection of the mandibular support and the posterior component to the anterior component and the anatomical contours of both the mandibular support and posterior component;

wherein the lower part defines a sternal support extending downwardly and commences below and beyond a lower periphery of the upper part, the sternal support being devoid of the tensioning device and the at least one cable, and wherein the at least one cable extends only to the lower periphery of the upper part relative to the vertical centerline and above the sternal support;

wherein the anterior component is arranged so that the mandibular support is fitted against a chin of a patient and extended in height to a chest of the patient with the sternal support;

wherein the tensioning device includes a dial and a spool, wherein the spool is arranged for winding and unwinding the at least one cable upon rotation of the dial;

wherein the cervical collar forms a tracheal opening centrally located on the anterior component, wherein the tracheal opening is defined in part by a peripheral segment of the upper part and a peripheral segment of the lower part, a height of the tracheal opening varying according to a length of the at least one cable, wherein the tensioning device is located on the upper part above the tracheal opening.

2. The cervical collar of claim 1, wherein the upper and lower parts are secured to one another at wing portions, the height adjustment of the anterior component occurring substantially more at a center portion than at the wing portions.

3. The cervical collar of claim 2, further comprising a height adjustment mechanism securing the wing portions to one another and permitting height adjustment of the wing portions relative to one another.

4. The cervical collar of claim 3, wherein the height adjustment mechanism includes a female component formed by the upper part and arranged generally parallel to the vertical centerline of the anterior component.

5. The cervical collar of claim 1, wherein the at least one cable includes first and second cable segments extending through a plurality of guides formed by the upper and lower parts for guiding the at least one cable on first and second sides of the anterior component from the vertical centerline.

6. The cervical collar of claim 5, wherein first and second ends of the first and second cable segments are received by the tensioning device, and the first and second cable segments continuously extend through the plurality of guides.

7. The cervical collar of claim 5, wherein due to adjustment of the tensioning device, a length of the first and second cable segments is reduced such that the at least one cable pulls a lower periphery of the lower part via one of the plurality of guides toward a lower periphery of the upper part to reduce the height of the anterior component.

8. The cervical collar of claim 1, wherein the upper part defines at least one retainer for securing the tensioning device thereto, the at least one retainer located along the peripheral segment intersected at a point along the vertical centerline such that the tensioning device is located above and adjacent to the at least one retainer.

9. The cervical collar of claim 8, wherein the at least one retainer defines at least one opening for guiding the at least one cable therethrough.

10. The cervical collar of claim 1, further comprising a plurality of guides formed by the upper and lower parts for guiding the at least one cable.

11. The cervical collar of claim 1, wherein the upper part forms upper and lower guides along an inner surface on an opposite side of an outer surface, the at least one cable arranged to slide within the upper and lower guides.

12. The cervical collar of claim 1, wherein the lower part forms a guide along an inner surface opposite an outer surface, the inner surface of the lower part opposing an inner surface of the upper part, such that the at least one cable routes between the inner surfaces of the upper and lower parts.

13. The cervical collar of claim 1, wherein the upper part has a central tab extending along the vertical centerline of the anterior component which secures the mandibular support.

14. The cervical collar of claim 1, further comprising first and second side height mechanisms arranged generally parallel to the vertical centerline and located at end portions of the upper and lower parts.

15. The cervical collar of claim 1, wherein an inner surface of the upper part slides over an inner surface of the lower part, the inner surface of the lower part being opposite an outer surface of the lower part arranged adjacent to the patient, the inner surface of the upper part being located opposite the outer surface of the upper part.

16. The cervical collar of claim 1, wherein the upper part forms upper and lower guides between upper and lower peripheral edges of the upper part, and the at least one cable extends solely between the upper and lower guides and does not extend below the lower peripheral edge of the upper part.

17. A cervical collar including an anterior component for coupling to a posterior component having an anatomical contour to circumferentially surround a neck, and a mandibular support having an anatomical contour and coupling to the anterior component, the anterior component defining a vertical centerline, the anterior component comprising:

an upper part arranged for receiving the mandibular support and having a central tab extending along the vertical centerline of the anterior component which secures the mandibular support;

a lower part connected to the upper part;

a single rotary tensioning device connected to the upper part and arranged along the vertical centerline;

at least one cable engaging between the upper and lower parts and arranged to be shortened or lengthened for height adjustment relative to the upper and lower parts by the single rotary tensioning device to move the lower part relative to the upper part;

wherein the height adjustment of the upper part relative to the lower part maintains the connection of the mandibular support and the posterior component to the anterior component and the anatomical contours of both the mandibular support and posterior component;

wherein the upper part forms at least one retainer for securing the single rotary tensioning device thereto, the at least one retainer located along a lower peripheral segment of the upper part and intersecting a point along the vertical centerline such that the single rotary tensioning device is located above and adjacent to the at least one retainer and adjacently below the central tab;

wherein the tensioning device is mounted on an outer surface of the upper part, and the tensioning device is rotatable around an axis perpendicular to and intersecting the vertical centerline;

wherein the tensioning device includes a dial and a spool, wherein the spool is arranged for winding and unwinding the at least one cable upon rotation of the dial;

wherein the cervical collar forms a tracheal opening centrally located on the anterior component, wherein the tracheal opening is defined in part by a peripheral segment of the upper part and a peripheral segment of the lower part, a height of the tracheal opening varying according to a length of the at least one cable, wherein the tensioning device is located on the upper part above the tracheal opening.

18. The cervical collar of claim 17, wherein the upper part forms upper and lower guides between upper and lower peripheral edges of the upper part, and the at least one cable extends solely between the upper and lower guides and does not extend below the lower peripheral edge of the upper part.

19. A cervical collar including an anterior component for coupling to a posterior component having an anatomical contour to circumferentially surround a neck, and a mandibular support having an anatomical contour and coupling to the anterior component, the anterior component defining a vertical centerline, the anterior component comprising:
- an upper part arranged for receiving the mandibular support and having a central tab extending along the vertical centerline of the anterior component which secures the mandibular support;
- a lower part connected to the upper part;
- a single rotary tensioning device connected to the upper part and arranged along the vertical centerline;
- a tracheal opening centrally located on the anterior component, the tracheal opening defined in part by a peripheral segment of the upper part and a peripheral segment of the lower part, a height of the tracheal opening varying according to a length of at least one cable;
- the at least one cable engaging between the upper and lower parts and arranged to be shortened or lengthened for height adjustment relative to the upper and lower parts by the single rotary tensioning device to move the lower part relative to the upper part;
- wherein the height adjustment of the upper part relative to the lower part maintains the connection of the mandibular support and the posterior component to the anterior component and the anatomical contours of both the mandibular support and posterior component;
- first and second side height mechanisms arranged generally parallel to the vertical centerline and located at end portions of the upper and lower parts;
- wherein the upper part forms at least one retainer for securing the single rotary tensioning device thereto, the at least one retainer located along the peripheral segment intersected along the vertical centerline such that the single rotary tensioning device is located above and adjacent to the at least one retainer and adjacently below the central tab;
- wherein the tensioning device is mounted on an outer surface of the upper part, the tensioning device is rotatable around an axis perpendicular to and intersecting the vertical centerline, and the tensioning device is located on the upper part above the tracheal opening;
- wherein the tensioning device includes a dial and a spool, wherein the spool is arranged for winding and unwinding the at least one cable upon rotation of the dial.

* * * * *